(12) United States Patent
Gane et al.

(10) Patent No.: US 10,294,371 B2
(45) Date of Patent: *May 21, 2019

(54) PROCESS FOR THE PRODUCTION OF NANO-FIBRILLAR CELLULOSE GELS

(71) Applicant: FiberLean Technologies Limited, Par Cornwall (GB)

(72) Inventors: Patrick A. C. Gane, Rothrist (CH); Joachim Schoelkopf, Killwangen (CH); Daniel Gantenbein, Elnesvagen (NO); Michel Schenker, Schönenwerd (CH)

(73) Assignee: FiberLean Technologies Limited, Par Cornwall (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/474,749

(22) Filed: Sep. 2, 2014

(65) Prior Publication Data

US 2014/0370179 A1 Dec. 18, 2014

Related U.S. Application Data

(63) Continuation of application No. 13/138,646, filed as application No. PCT/EP2010/054233 on Mar. 30, 2010, now Pat. No. 8,871,056.

(Continued)

(30) Foreign Application Priority Data

Mar. 30, 2009 (EP) .................................. 09156703

(51) Int. Cl.
*C08L 97/02* (2006.01)
*B82Y 30/00* (2011.01)
(Continued)

(52) U.S. Cl.
CPC ............. *C08L 97/02* (2013.01); *A23L 29/262* (2016.08); *B82Y 30/00* (2013.01); *C08J 3/00* (2013.01);
(Continued)

(58) Field of Classification Search
CPC ..... C08K 2003/265; C08K 3/26; C08L 97/02; D21H 11/18
See application file for complete search history.

(56) References Cited

U.S. PATENT DOCUMENTS 57,307 A 8/1866 Fletcher
168,783 A 10/1875 Riley
(Continued)

FOREIGN PATENT DOCUMENTS

BE 1006908 A3 1/1995
CA 1096676 A 3/1981
(Continued)

OTHER PUBLICATIONS

Turbak, A. F., "Birth of nanocellulose," http://www.naylornetwork.com/PPI-OTW/articles/print.asp?aid=150993, undated, downloaded Nov. 1, 2015.*

(Continued)

*Primary Examiner* — Nicholas E Hill
(74) *Attorney, Agent, or Firm* — Pierce Atwood LLP; Raymond G. Arner

(57) ABSTRACT

The present invention relates to a process for the production of nano-fibrillar cellulose gels by providing cellulose fibers and at least one filler and/or pigment; combining the cellulose fibers and the at least one filler and/or pigment; and fibrillating the cellulose fibers in the presence of the at least one filler and/or pigment until a gel is formed, as well as the nano-fibrillar cellulose gel obtained by this process and uses thereof.

21 Claims, 8 Drawing Sheets

Related U.S. Application Data

(60) Provisional application No. 61/212,073, filed on Apr. 6, 2009.

(51) Int. Cl.

| | |
|---|---|
| *C08J 3/00* | (2006.01) |
| *C08J 3/075* | (2006.01) |
| *C08J 5/00* | (2006.01) |
| *D01D 5/42* | (2006.01) |
| *D01F 2/00* | (2006.01) |
| *D21B 1/04* | (2006.01) |
| *D21B 1/30* | (2006.01) |
| *D21C 9/00* | (2006.01) |
| *C08K 3/26* | (2006.01) |
| *C08L 33/02* | (2006.01) |
| *C08L 33/08* | (2006.01) |
| *C08L 33/26* | (2006.01) |
| *C08L 67/00* | (2006.01) |
| *C08L 85/02* | (2006.01) |
| *A23L 29/262* | (2016.01) |
| *C09D 101/00* | (2006.01) |

(52) U.S. Cl.
CPC ............... *C08J 3/075* (2013.01); *C08J 5/005* (2013.01); *C08K 3/26* (2013.01); *C08L 33/02* (2013.01); *C08L 33/08* (2013.01); *C08L 33/26* (2013.01); *C08L 67/00* (2013.01); *C08L 85/02* (2013.01); *C09D 101/00* (2013.01); *D01D 5/423* (2013.01); *D01F 2/00* (2013.01); *D21B 1/04* (2013.01); *D21B 1/30* (2013.01); *D21C 9/004* (2013.01); *D21C 9/007* (2013.01); *A23V 2002/00* (2013.01); *C08K 2003/265* (2013.01)

(56) References Cited

U.S. PATENT DOCUMENTS

| | | |
|---|---|---|
| 1,538,257 A | 5/1925 | Obrecht |
| 2,006,209 A | 5/1933 | Bradner |
| 2,169,473 A | 2/1935 | Olsen et al. |
| 2,583,548 A | 1/1952 | Lutton et al. |
| 3,075,710 A | 1/1963 | Feld et al. |
| 3,730,830 A | 5/1973 | Driscoll |
| 3,765,921 A | 10/1973 | Puskar |
| 3,794,558 A | 2/1974 | Back |
| 3,820,548 A | 6/1974 | Buchmann et al. |
| 3,921,581 A | 11/1975 | Brewer |
| 4,026,762 A | 5/1977 | Bauman |
| 4,087,317 A | 5/1978 | Roberts |
| 4,167,548 A | 9/1979 | Arduini et al. |
| 4,229,250 A | 10/1980 | Lehtinen |
| 4,275,084 A | 6/1981 | Ohyabu et al. |
| 4,285,842 A | 8/1981 | Herr |
| 4,318,959 A | 3/1982 | Evans et al. |
| 4,341,807 A | 7/1982 | Turbak et al. |
| 4,356,060 A | 10/1982 | Neckermann et al. |
| 4,374,702 A | 2/1983 | Turbak et al. |
| 4,378,381 A | 3/1983 | Turbak et al. |
| 4,426,258 A | 1/1984 | Browning |
| 4,452,721 A | 6/1984 | Turbak et al. |
| 4,452,722 A | 6/1984 | Turbak et al. |
| 4,460,737 A | 8/1984 | Evans et al. |
| 4,464,287 A | 8/1984 | Turbak et al. |
| 4,474,949 A | 10/1984 | Chatterjee et al. |
| 4,481,076 A | 11/1984 | Herrick |
| 4,481,077 A | 11/1984 | Herrick |
| 4,487,634 A | 12/1984 | Turbak et al. |
| 4,495,245 A | 1/1985 | Zunker |
| 4,500,546 A | 2/1985 | Turbak et al. |
| 4,510,020 A | 4/1985 | Green et al. |
| 4,705,712 A | 11/1987 | Cashaw et al. |
| 4,744,987 A | 5/1988 | Mehra et al. |
| 4,761,203 A | 8/1988 | Vinson |
| 4,820,813 A | 4/1989 | Schultz |
| 4,889,594 A | 12/1989 | Gavelin |
| 4,952,278 A | 8/1990 | Gregory et al. |
| 5,009,886 A | 4/1991 | Ahmad et al. |
| 5,098,520 A | 3/1992 | Begala |
| 5,104,411 A | 4/1992 | Makoui et al. |
| 5,123,962 A | 6/1992 | Komuro et al. |
| 5,156,719 A | 10/1992 | Passaretti |
| 5,223,090 A | 6/1993 | Klungness et al. |
| 5,227,024 A | 6/1993 | Gomez |
| 5,225,041 A | 7/1993 | Richard et al. |
| 5,228,900 A | 7/1993 | Stephens et al. |
| 5,240,561 A | 8/1993 | Kaliski |
| 5,244,542 A | 9/1993 | Bown et al. |
| 5,269,470 A | 12/1993 | Ishikawa et al. |
| 5,274,199 A | 12/1993 | Uryu et al. |
| 5,279,663 A | 1/1994 | Kaliski |
| 5,312,484 A | 1/1994 | Kaliski |
| 5,290,830 A | 3/1994 | Tung et al. |
| 5,316,621 A | 5/1994 | Kitao et al. |
| 5,385,640 A | 1/1995 | Weibel et al. |
| 5,443,902 A | 1/1995 | Knox et al. |
| 5,387,319 A | 2/1995 | Mora et al. |
| 5,487,419 A | 1/1996 | Weibel |
| 5,531,821 A | 7/1996 | Wu |
| 5,605,568 A | 2/1997 | Naydowski et al. |
| 5,670,623 A | 9/1997 | Shoseyov et al. |
| 5,731,080 A * | 3/1998 | Cousin .................. D21H 11/18 106/464 |
| 5,840,320 A | 3/1998 | Odom |
| 5,817,381 A | 11/1998 | Chen et al. |
| 5,837,376 A | 11/1998 | Knox et al. |
| 5,964,983 A | 10/1999 | Dinand et al. |
| 6,037,380 A | 3/2000 | Venables et al. |
| 6,074,524 A | 3/2000 | Wu et al. |
| 6,083,317 A * | 7/2000 | Snowden ................ C09C 1/024 106/464 |
| 6,083,582 A | 7/2000 | Chen et al. |
| 6,117,305 A | 9/2000 | Bando et al. |
| 6,117,474 A | 9/2000 | Kamada et al. |
| 6,117,545 A | 9/2000 | Cavaille et al. |
| 6,117,804 A | 9/2000 | Cho |
| 6,132,558 A | 10/2000 | Dyllick-Brenzinger et al. |
| 6,156,118 A | 12/2000 | Silenius |
| 6,159,335 A | 12/2000 | Owens et al. |
| 6,183,596 B1 | 2/2001 | Matsuda et al. |
| 6,202,946 B1 | 3/2001 | Virtanen |
| 6,207,436 B1 * | 3/2001 | Bjørnvad ............... C11D 3/001 435/183 |
| 6,214,163 B1 | 4/2001 | Matsuda et al. |
| 6,235,150 B1 | 5/2001 | Middleton et al. |
| 6,312,669 B1 | 11/2001 | Cantiani et al. |
| 6,339,898 B1 | 1/2002 | Toye |
| 6,379,594 B1 | 4/2002 | Dopfner et al. |
| 6,436,232 B1 | 8/2002 | Silenius et al. |
| 6,468,393 B1 | 10/2002 | Small et al. |
| 6,579,410 B1 | 6/2003 | Bleakley et al. |
| 6,604,698 B2 | 8/2003 | Verhoff et al. |
| 6,647,662 B2 | 11/2003 | Toye |
| 6,669,882 B2 | 12/2003 | Seok |
| 6,706,876 B2 | 3/2004 | Luo et al. |
| 6,726,807 B1 | 4/2004 | Mathur |
| 6,787,497 B2 | 9/2004 | Dellve et al. |
| 6,861,081 B2 | 3/2005 | Weibel |
| 7,022,756 B2 | 4/2006 | Singer |
| 7,048,900 B2 | 5/2006 | Mathur et al. |
| 7,083,703 B2 | 8/2006 | Aho et al. |
| 7,169,258 B2 | 1/2007 | Rheims et al. |
| 7,179,347 B2 | 2/2007 | Rheims et al. |
| 7,285,182 B2 | 10/2007 | Mason et al. |
| 7,381,294 B2 | 6/2008 | Suzuki et al. |
| 7,459,493 B2 | 12/2008 | Singer |
| 7,462,232 B2 | 12/2008 | Tuason et al. |
| 7,497,924 B2 | 3/2009 | Nguyen et al. |
| 7,594,619 B2 | 9/2009 | Ghere, Jr. et al. |
| 7,726,592 B2 | 6/2010 | Fernandez et al. |
| 7,790,276 B2 | 9/2010 | Kanakarajan |
| 7,799,358 B2 | 9/2010 | Weibel |
| 8,012,312 B2 | 9/2011 | Goto et al. |

(56) References Cited

U.S. PATENT DOCUMENTS

| | | |
|---|---|---|
| 8,012,573 B2 | 9/2011 | Kowata et al. |
| 8,231,764 B2 | 7/2012 | Husband et al. |
| 8,871,056 B2 | 10/2014 | Gane et al. |
| 8,871,057 B2 | 10/2014 | Gane et al. |
| 9,157,189 B2 | 10/2015 | Heiskanen et al. |
| 9,175,442 B2 | 11/2015 | Gene et al. |
| 9,399,838 B2 | 7/2016 | Laine et al. |
| 2001/0011516 A1 | 8/2001 | Cantiani et al. |
| 2001/0045264 A1 | 11/2001 | Rheims et al. |
| 2002/0031592 A1 | 3/2002 | Weibel |
| 2002/0059886 A1 | 5/2002 | Merkley et al. |
| 2002/0198293 A1 | 12/2002 | Craun et al. |
| 2003/0051841 A1 | 3/2003 | Mathur et al. |
| 2003/0094252 A1 | 5/2003 | Sundar et al. |
| 2003/0114641 A1 | 6/2003 | Kelly et al. |
| 2004/0108081 A1 | 6/2004 | Hughes |
| 2004/0131854 A1 | 7/2004 | Aho et al. |
| 2004/0146605 A1 | 7/2004 | Weibel |
| 2004/0149403 A1 | 8/2004 | Rheims et al. |
| 2004/0168782 A1 | 9/2004 | Silenius et al. |
| 2004/0168783 A1* | 9/2004 | Munchow ............... D21H 19/00 162/189 |
| 2004/0173329 A1 | 9/2004 | Silenius et al. |
| 2004/0226671 A1 | 11/2004 | Nguyen et al. |
| 2005/0000665 A1 | 1/2005 | Doelle |
| 2005/0045288 A1 | 3/2005 | Riou |
| 2005/0051054 A1 | 3/2005 | White et al. |
| 2005/0089601 A1 | 4/2005 | Weibel |
| 2005/0103459 A1 | 5/2005 | Mathur |
| 2005/0116010 A1 | 6/2005 | Gronroos et al. |
| 2005/0133643 A1 | 6/2005 | Fernandez et al. |
| 2005/0194477 A1* | 9/2005 | Suzuki .................... D21D 1/30 241/20 |
| 2005/0256262 A1 | 11/2005 | Hill et al. |
| 2006/0078647 A1 | 4/2006 | Weibel |
| 2006/0201646 A1 | 9/2006 | Gussinyer Canadell |
| 2006/0266485 A1 | 11/2006 | Knox et al. |
| 2006/0280839 A1 | 12/2006 | Weibel |
| 2006/0289132 A1 | 12/2006 | Heijnesson-Hulten |
| 2007/0062009 A1 | 3/2007 | Ghere, Jr. et al. |
| 2007/0131361 A1 | 6/2007 | Doelle et al. |
| 2007/0148365 A1 | 6/2007 | Knox et al. |
| 2007/0224419 A1 | 9/2007 | Sumnicht et al. |
| 2007/0226919 A1 | 10/2007 | Mheidle |
| 2007/0231568 A1 | 10/2007 | Kanakarajan |
| 2007/0272376 A1 | 11/2007 | Maijala et al. |
| 2008/0023161 A1 | 1/2008 | Gather |
| 2008/0057307 A1 | 3/2008 | Koslow et al. |
| 2008/0060774 A1 | 3/2008 | Zuraw et al. |
| 2008/0146701 A1 | 6/2008 | Sain et al. |
| 2008/0210391 A1 | 9/2008 | Pfalzer et al. |
| 2008/0265222 A1 | 10/2008 | Ozersky et al. |
| 2009/0020139 A1 | 1/2009 | Sumnicht et al. |
| 2009/0020248 A1 | 1/2009 | Sumnicht et al. |
| 2009/0065164 A1 | 3/2009 | Goto et al. |
| 2009/0084874 A1 | 4/2009 | Alam et al. |
| 2009/0221812 A1 | 9/2009 | Ankerfors et al. |
| 2010/0024998 A1 | 2/2010 | Wildlock et al. |
| 2010/0059191 A1 | 3/2010 | Garcia Melgarejo et al. |
| 2010/0132901 A1 | 6/2010 | Wild |
| 2010/0139527 A1 | 6/2010 | Fernandez-Garcia |
| 2010/0212850 A1 | 8/2010 | Sumnicht et al. |
| 2010/0233468 A1 | 9/2010 | Ioelovich et al. |
| 2010/0272938 A1 | 10/2010 | Mitchell et al. |
| 2010/0272980 A1 | 10/2010 | Kowata et al. |
| 2011/0081554 A1 | 4/2011 | Ankerfors et al. |
| 2011/0088860 A1 | 4/2011 | Heijnesson-Hulten et al. |
| 2011/0114765 A1 | 5/2011 | Brady et al. |
| 2011/0186252 A1 | 8/2011 | Subramanian et al. |
| 2011/0223401 A1 | 9/2011 | Harlin et al. |
| 2011/0259537 A1 | 10/2011 | Husband et al. |
| 2011/0274908 A1 | 11/2011 | Kowata et al. |
| 2011/0277947 A1 | 11/2011 | Hua et al. |
| 2012/0043039 A1 | 2/2012 | Paltakari et al. |
| 2012/0094953 A1 | 4/2012 | Gane et al. |
| 2012/0107480 A1 | 5/2012 | Gane et al. |
| 2012/0125547 A1 | 5/2012 | Akai et al. |
| 2012/0132383 A1 | 5/2012 | Laine et al. |
| 2012/0205065 A1 | 8/2012 | Esser |
| 2012/0216718 A1 | 8/2012 | Berglund et al. |
| 2012/0277351 A1 | 11/2012 | Yano et al. |
| 2012/0318471 A1 | 12/2012 | Turkki et al. |
| 2013/0000855 A1 | 1/2013 | Nuopponen et al. |
| 2013/0017349 A1 | 1/2013 | Heiskanen et al. |
| 2013/0053454 A1 | 2/2013 | Heiskanen et al. |
| 2013/0126112 A1 | 5/2013 | Gane et al. |
| 2013/0131193 A1 | 5/2013 | Gane et al. |
| 2013/0133848 A1 | 5/2013 | Heijnesson-Holten et al. |
| 2013/0180680 A1 | 7/2013 | Axrup et al. |
| 2013/0284387 A1 | 10/2013 | Umemoto et al. |
| 2013/0345416 A1 | 12/2013 | Laukkanen et al. |
| 2014/0058077 A1 | 2/2014 | Laukkanen et al. |
| 2014/0302337 A1 | 10/2014 | Gane et al. |
| 2014/0345816 A1 | 11/2014 | Heiskanen et al. |
| 2014/0370179 A1 | 12/2014 | Gane et al. |
| 2014/0371172 A1 | 12/2014 | Gane et al. |
| 2015/0101769 A1 | 4/2015 | Laine et al. |
| 2015/0101770 A1 | 4/2015 | Laine et al. |
| 2015/0144279 A1 | 5/2015 | Laine et al. |
| 2015/0330024 A1 | 11/2015 | Gane et al. |
| 2016/0273165 A1 | 9/2016 | Laine et al. |
| 2016/0299119 A1 | 10/2016 | Laukkanen et al. |

FOREIGN PATENT DOCUMENTS

| | | |
|---|---|---|
| CA | 1149219 A | 7/1983 |
| CA | 1162819 A | 2/1984 |
| CA | 2292587 A1 | 12/1998 |
| CA | 2093545 C | 3/2001 |
| CA | 2437616 A1 | 2/2005 |
| CA | 2750082 A1 | 8/2010 |
| CH | 648071 A | 2/1985 |
| CN | 85108131 A | 5/1987 |
| CN | 1089675 A | 7/1994 |
| CN | 1173904 A | 2/1998 |
| CN | 1200128 A | 11/1998 |
| CN | 1278830 A | 1/2001 |
| CN | 2437616 Y | 7/2001 |
| CN | 1524145 A | 8/2004 |
| CN | 1585839 A1 | 2/2005 |
| CN | 101360863 A | 2/2005 |
| CN | 1665984 A | 9/2005 |
| CN | 101203644 A | 6/2008 |
| CN | 102869831 B1 | 9/2015 |
| DK | 175143 B1 | 6/2004 |
| EP | 51230 A1 | 5/1982 |
| EP | 39628 B1 | 7/1984 |
| EP | 0198622 A1 | 10/1986 |
| EP | 273745 A2 | 7/1988 |
| EP | 442183 A1 | 8/1991 |
| EP | 492600 A1 | 7/1992 |
| EP | 499578 A1 | 8/1992 |
| EP | 0614948 A1 | 9/1994 |
| EP | 619140 A2 | 10/1994 |
| EP | 0625611 A1 | 11/1994 |
| EP | 0726356 A1 | 8/1996 |
| EP | 579171 B1 | 1/1997 |
| EP | 785307 A2 | 7/1997 |
| EP | 790135 A2 | 8/1997 |
| EP | 619140 B1 | 5/1999 |
| EP | 0935020 A1 | 8/1999 |
| EP | 0949294 A1 | 10/1999 |
| EP | 988322 81 | 1/2002 |
| EP | 1053213 B1 | 5/2002 |
| EP | 0785307 B1 | 9/2002 |
| EP | 0852588 | 1/2003 |
| EP | 1469126 A1 | 10/2004 |
| EP | 1538257 | 6/2005 |
| EP | 1538257 A1 | 6/2005 |
| EP | 1936032 A1 | 6/2008 |
| EP | 2196579 A1 | 6/2010 |
| EP | 2216345 A1 | 8/2010 |
| EP | 2236545 A1 | 10/2010 |
| EP | 2236664 A1 | 10/2010 |

(56) References Cited

FOREIGN PATENT DOCUMENTS

| | | |
|---|---|---|
| EP | 1907626 B1 | 11/2010 |
| EP | 2386682 B1 | 11/2011 |
| EP | 2386683 B1 | 3/2014 |
| EP | 2563967 B1 | 8/2017 |
| EP | 2640893 B1 | 8/2017 |
| ES | 2100781 A1 | 6/1997 |
| FR | 2689530 A1 | 10/1993 |
| FR | 2774702 A1 | 8/1999 |
| GB | 663621 | 12/1951 |
| GB | 2260146 A | 4/1993 |
| GB | 2265916 A | 10/1993 |
| GB | 2275876 A | 9/1994 |
| GB | 2528487 A | 1/2016 |
| JP | 1-156587 A | 6/1989 |
| JP | H04-81813 A | 7/1992 |
| JP | H0598589 A | 4/1993 |
| JP | 6-158585 A | 6/1994 |
| JP | 06-240588 A | 8/1994 |
| JP | 8-81896 A | 3/1996 |
| JP | 2528487 B2 | 8/1996 |
| JP | 8-284090 A | 10/1996 |
| JP | 199608284090 A | 10/1996 |
| JP | 9-124702 A | 5/1997 |
| JP | 10158303 A | 6/1998 |
| JP | 10-237220 A | 9/1998 |
| JP | 11-269796 A | 10/1999 |
| JP | 2976485 B2 | 11/1999 |
| JP | 2981555 B1 | 11/1999 |
| JP | 2000-170029 A | 6/2000 |
| JP | 3421446 B2 | 6/2003 |
| JP | 2004231796 A | 8/2004 |
| JP | 2004523676 A | 8/2004 |
| JP | 2004-534911 A | 11/2004 |
| JP | 2005505708 A | 2/2005 |
| JP | 2006008857 A | 1/2006 |
| JP | 2007262594 A | 10/2007 |
| JP | 2008007899 A | 1/2008 |
| JP | 2008150719 A | 7/2008 |
| JP | 2008169497 A | 7/2008 |
| JP | 2009161613 A | 7/2009 |
| JP | 2009243014 A | 10/2009 |
| JP | 2009263854 A | 11/2009 |
| JP | 2010168716 A | 8/2010 |
| JP | 2010-202987 A | 9/2010 |
| JP | 2010202987 A | 9/2010 |
| JP | 2012-522145 A | 9/2012 |
| JP | 5666553 B2 | 2/2015 |
| JP | 5894525 B2 | 3/2016 |
| KR | 20080096747 A | 11/2008 |
| NL | 8102857 A | 1/1983 |
| RU | 2208079 C2 | 7/2003 |
| RU | 2345189 C2 | 1/2009 |
| SU | 499366 A1 | 1/1977 |
| TW | 200609278 | 3/2006 |
| TW | 200609278 A | 3/2006 |
| TW | 201013017 A1 | 4/2010 |
| WO | 93001333 A1 | 1/1993 |
| WO | 9315270 A1 | 8/1993 |
| WO | 94/05595 A1 | 3/1994 |
| WO | 9404745 A1 | 3/1994 |
| WO | 97/12917 A1 | 4/1997 |
| WO | 9712917 A1 | 4/1997 |
| WO | 9718897 A2 | 5/1997 |
| WO | 98/28362 A1 | 7/1998 |
| WO | 98/56860 A2 | 12/1998 |
| WO | 9855693 A1 | 12/1998 |
| WO | 9856826 A1 | 12/1998 |
| WO | 9856860 A1 | 12/1998 |
| WO | 98056860 A2 | 12/1998 |
| WO | 9954045 A1 | 10/1999 |
| WO | 0166600 A1 | 9/2001 |
| WO | 0198231 A1 | 12/2001 |
| WO | 02086238 A1 | 10/2002 |
| WO | 02090651 A1 | 11/2002 |
| WO | 02/100955 A1 | 12/2002 |
| WO | 02100955 A1 | 12/2002 |
| WO | 03033815 A2 | 4/2003 |
| WO | 2004/016852 A1 | 2/2004 |
| WO | 2004/055267 A1 | 7/2004 |
| WO | 2005/014934 A2 | 2/2005 |
| WO | 2005/061793 A1 | 7/2005 |
| WO | 2005/100489 A1 | 10/2005 |
| WO | 2005/123840 A1 | 12/2005 |
| WO | 2006/009502 A1 | 1/2006 |
| WO | 2006/041401 A1 | 4/2006 |
| WO | 2006/136651 A1 | 12/2006 |
| WO | 2007/006794 A1 | 1/2007 |
| WO | 2007/091942 A1 | 8/2007 |
| WO | 2007/096180 A2 | 8/2007 |
| WO | 2007088974 A1 | 8/2007 |
| WO | 2007/110639 A1 | 10/2007 |
| WO | 2008/008576 A2 | 1/2008 |
| WO | 2008/033283 A1 | 3/2008 |
| WO | 2008/076056 A1 | 6/2008 |
| WO | 2008/076071 A1 | 6/2008 |
| WO | 2008/095764 A1 | 8/2008 |
| WO | 2008132228 A1 | 11/2008 |
| WO | 2009074491 A1 | 6/2009 |
| WO | 2009/123560 A1 | 10/2009 |
| WO | 2009122982 A1 | 10/2009 |
| WO | 2009126106 A1 | 10/2009 |
| WO | 2009153225 A1 | 12/2009 |
| WO | 2010/003860 A2 | 1/2010 |
| WO | 2010/015726 A1 | 2/2010 |
| WO | 2010015726 A1 | 2/2010 |
| WO | 2010/092239 A1 | 8/2010 |
| WO | 2010092239 A1 | 8/2010 |
| WO | 2010102802 A1 | 9/2010 |
| WO | 201012519 | 10/2010 |
| WO | 2010112519 A1 | 10/2010 |
| WO | 2010115785 | 10/2010 |
| WO | 2010115785 A1 | 10/2010 |
| WO | 2010/131016 A2 | 11/2010 |
| WO | 2010125247 A2 | 11/2010 |
| WO | 2010131016 A2 | 11/2010 |
| WO | 2011004300 A1 | 1/2011 |
| WO | 2011004301 A1 | 1/2011 |
| WO | 2011/042607 A1 | 4/2011 |
| WO | 2011/048000 A1 | 4/2011 |
| WO | 2011/056130 A1 | 5/2011 |
| WO | 2011/059398 A1 | 5/2011 |
| WO | 2011/068457 A1 | 6/2011 |
| WO | 2011064441 A1 | 6/2011 |
| WO | 2011/134938 A1 | 11/2011 |
| WO | 2011/134939 A1 | 11/2011 |
| WO | 2011/141876 A1 | 11/2011 |
| WO | 2011/141877 A1 | 11/2011 |
| WO | 2011134938 A1 | 11/2011 |
| WO | 2011134939 A1 | 11/2011 |
| WO | 2011/154335 A1 | 12/2011 |
| WO | 2012/039668 A1 | 3/2012 |
| WO | 2012098296 A2 | 7/2012 |
| WO | 2014091212 A1 | 6/2014 |

OTHER PUBLICATIONS

Ducheyne, Paul, et al., eds. Comprehensive biomaterials. vol. 1. Newnes, 2015, p. 409.*

Martin Rangnar, et al., "Pulp," Ullmann's Encyclopedia of Industrial Chemistry, published online 2000, 89 pages.*

Third Party Observations dated Jun. 11, 2012 for European Application No. 10161166.3.

The Communication from the European Patent Office dated Aug. 6, 2013 for European Application 11716257.8.

The Response to the Communication dated Nov. 5, 2013 or European Application No. 11716257.8.

Third Party Observations dated May 18, 2011 for European Application No. 09156683.6.

Third Party Observations dated Jan. 9, 2012 for European Application No. 10161173.9.

Third Party Observations dated Jun. 11, 2012 for European Application No. 10161173.9.

(56) References Cited

OTHER PUBLICATIONS

Third Party Observations dated Apr. 12, 2013 for European Application No. 10161173.9.
European Search Report dated Jun. 26, 2009 for European Application No. EP 09156683.6.
The International Search Report dated Nov. 3, 2011 for PCT Application No. PCT/EP2011/056540.
The Written Opinion of the International Searching Authority dated Oct. 27, 2012 for PCT Application No. PCT/EP2011/056540.
The Office Action dated Jan. 28, 2014 for Japanese Application No. 2012-502646.
The Examination Report dated Feb. 11, 2014 for Taiwanese Application No. 099109562.
The First Office Action dated Oct. 23, 2013 for Chinese Application No. 201080015263.x.
The Office Action dated Mar. 30, 2010 for Russian Application No. 2011143811.
The Office Action for Russian Application No. 2011143854.
The Office Action dated Jan. 7, 2014 for Canadian Application No. 2,755,495.
The Office Action for Ukrainian Application No. a 2011 12682.
Third Party Observation dated Jun. 6, 2012 for European Application No. 09156683.6.
Third Party Observation dated Oct. 21, 2011 for European Application No. 09156683.6.
European Search Opinion dated Jun. 26, 2009 for European Application No. 09156683.6.
European Search Report dated Jun. 26, 2009 for European Application No. 09156683.6.
Third Party Observation dated Jun. 6, 2012 for European Application No. 09156703.2.
Third Party Observation dated May 18, 2011 for European Application No. 09156703.2.
European Search Opinion dated Jun. 26, 2009 for European Application No. 09156703.2.
European Search Report dated Jun. 26, 2009 for European Application No. 09156703.2.
The International Search Report dated Oct. 7, 2010 for PCT Application No. PCT/EP2010/054231.
The Written Opinion of the International Searching Authority dated Sep. 30, 2011 for PCT Application No. PCT/EP2010/054231.
Shen et al. "Carbohydrate-based fillers and pigments for papermaking: A Review", 2011—Carbohydrate Polymers vol. 85, 17-22.
Chauhan et al. "Use of Nanotechnology for high performance cellulosic and papermaking products", 2002, Cellulose Chemistry and Technology, 46 (5-6), pp. 389-400.
Charani et al. "Rheological characterization of high concentrated MFC get from kenaf unbleached pulp", 2013, Celulose, vol. 20, pp. 727-740.
Opietnik et al. Tencel® Gel—A novel Cellulose Micro Suspension, 2013, Lenzinger Berichte, vol. 91, pp. 89-92.
Third Party Observations dated Jun. 11, 2012 for European Application No. EP 10713884.4.
Third Party Observations dated Feb. 17, 2012 for European Application No. EP 10713884.4.
Third Party Observations dated Jun. 11, 2012 for European Application No. EP 10711423.3.
Third Party Observations dated Feb. 17, 2012 for European Application No. EP 10711423.3.
Third Party Observations dated Jan. 9, 2012 for European Application No. EP 10161166.3.
Third Party Observations dated Apr. 12, 2013 for European Application No. EP 10161166.3.
Third Party Observations dated Feb. 4, 2013 for European Application No. EP 11716257.
Third Party Observations dated Feb. 4, 2013 for European Application No. EP 11719499.
The Office Action dated Jan. 2, 2014 for European Application No. 10713884.4.
The Office Action dated Feb. 21, 2013 for European Application No. 10713884.4.
The Office Action dated Jan. 2, 2014 for European Application No. 09156683.6.
The Office Action dated Jul. 31, 2013 for European Application No. 09156683.6.
The Office Action dated Feb. 7, 2013 for European Application No. 09156683.6.
The Office Action dated Jun. 27, 2011 for European Application No. 09156683.6.
The Office Action dated Jul. 31, 2013 for European Application No. 09156703.2.
The Office Action dated Feb. 7, 2013 for European Application No. 09156703.2.
The Office Action dated May 20, 2011 for European Application No. 09156703.2.
The Office Action dated Mar. 26, 2014 for European Application No. 10711423.3.
The Office Action dated Sep. 24, 2012 for European Application No. 10711423.3.
The Office Action dated Mar. 15, 2013 for European Application No. 10161166.3.
The European Search Report dated Sep. 8, 2010 for European Application No. 10161166.3.
The Office Action dated Aug. 6, 2013 for European Application No. 11716257.
The Office Action dated Feb. 15, 2013 for European Application No. 11716257.
The Office Action dated Mar. 15, 2013 for European Application No. 10161173.9.
The European Search Report dated Sep. 7, 2010 for European Application No. 10161173.9.
The Office Action dated Oct. 11, 2013 for European Application No. 11719499.
The Office Action dated Jan. 16, 2013 for Chinese Application No. 201080015262.5.
Little et al. "Hydrated Lime—more than just a filler." National Lime Association.
Dupont "Cellulose in lithium chloride/N,N-dimethylacetamide, optimisation of a disollution method using paper substrates and stability of the solutions." Plymer 2003:44, 4117-4126.
Patt et al. "Paper and Pulp." Ullmann's Encyclopedia of Industrial Chemistry. Published online Jun. 2000.
Hubbe "Mini-encyclopedia of papermaking wet-end chemistry: Fibrillation." NC State University Internet Citation p. 1.
Hubbe et al. "What happens to cellulosic fibers during papermaking and recycling? A Review." BioResources 3(4) 739-788.
Siró et al. "Microfibrillated cellulose and new nanocomposite materials: A Review." Cellulose (2010) 17:459-494.
The International Search Report dated Aug. 17, 2010 for PCT Application No. PCT/EP2010/054233.
The Written Opinion for the International Searching Authority for PCT Application No. PCT/EP2010/054233.
Sixta "Handbook of Pulp." Wood Structure and Morphology, vol. 1, pp. 41 and 42.
Third Party Observations dated Oct. 21, 2011 for European Application No. EP 09156703.2.
Third Party Observations dated Jun. 26, 2009 for European Application No. EP 09156703.2.
Falini et al. "Oriented cyrystallization of vaterite in collagenous matrices." Chem. Eur. J. 1998, 4, 1048-1052.
de Oliveira et al., "Synthesis and Characterization of Microcrystalline Cellulose Produced from Bacterial Cellulose," J. Therm. Anal. Calorim, (2011) 106, pp. 703-709.
Herrick et al., "Microfibrillated, Cellulose: Morphology and Accessibility," Journal of Applied Polymer Science: Applied Polymer Symposium, (1983) 37, pp. 797-813.
Kumar et al., "Comparison of Nano- and Microfibrillated Cellulose Films," Cellulose, (2014) 21, pp. 3443-3456.
Pääkkö et al., "Enzymatic Hydrolysis Combined with Mechanical Shearing and High-Pressure Homogenization for Nanoscale Cellulose Fibrils and Strong Gels." Biomacromolecules, (2007) 8, pp. 1934-1941.

(56) References Cited

OTHER PUBLICATIONS

Postek et al., "Production and Applications of Cellulose Nanomaterials," TAPPI Press (2013) Chapter 2, pp. 169-173.
Sofia et al., "A Comparision of Cellulose Nanocrystals and Cellulose Nanofibres Extracted from Bagasse Using Acid and Ball Milling Methods," Adv. Nat. Sci.: Nanosci. Nanotechnol., (2016) 7, 9 pages.
Janardhnan, et al. "Isolation of Cellulose Microfibrils—An Enzymatic Approach", BioResources, vol. 1, No. 2, 2006, pp. 176-188.
Japanese Notice of Rejection dated Mar. 31, 2015 for Japanese Patent Application No. 2013-506620, 9 pages.
Indonesia, Examination Report dated Oct. 13, 2015 for Indonesia Patent Application No. W00201103474, 4 pages.
Japanese Office Action dated Apr. 15, 2014 for Japananese Patent No. 2012-502647, 12 pages.
Japanese Office Action dated Dec. 8, 2015 for Japanese Patent Application No. 2014-248634, 8 pages.
Notice of Opposition dated Dec. 19, 2014 for European Patent No. EP238682, 22 pages.
Japanese Office Action dated Nov. 29, 2016 for Japanese Patent Application No. 2015-159928, 11 pages.
Japanese Office Action dated Oct. 20, 2015 for Japanese Patent No. 2012-502647, 3 pages.
Japanese Official Action dated Oct. 27, 2015 for Japanese Patent Application No. 2013-506620, 4 pages.
Japanese Office Action dated Dec. 1, 2015 for Japanese Patent Application No. 2013-506621, 5 pages.
Japanese Office Action dated Mar. 31, 2015 for Japanese Patent Application No. 2013-506621, 8 pages.
Kang, Taegeun, "Role of External Fibrillation in Pulp and Paper Properties," Doctoral Thesis, Helsinki University of Technology, Laboratory of Paper and Printing Technology Reports, Series A28, Espoo 2007, 50 pages.
Klemm, et al. "Nanocelluloses as Innovative Polymers in Research and Application", Adv. Polymer Science, vol. 205, 2006, pp. 49-96.
Klungness, et al. "Fiber-Loading: A Progress Report", TAPPI Proceedings, 1994 Recycling Symposium, pp. 283-290.
Korean Notice of Rejection for Korean Patent Application No. 10-2015-7030983 dated Jul. 29, 2016, 16 pages.
Korean Office Action dated Feb. 20, 2017 for Korean Patent Application No. 10-2016-7030178, 7 pages.
Korean Office Action dated Jan. 27, 2016 for Korean Patent Application No. 10-2011-7025315, 13 pages.
Korean Office Action dated Jul. 29, 2016f or Korean Patent Application No. 10-2012-7030744, 11 pages.
Korea, Office Action dated Mar. 28, 2016 for Korean Patent Application No. 10-2011-7025318, 12 pages.
Korean Office Action dated Jul. 29, 2016 for Korean Patent Application No. 10-2012-7030761, 13 pages.
Littiunen, Kuisma, "Free radical graft copolymerization of microfibrillated cellulose", Master's Thesis, Helsinki University of Technology, Sep. 2009, 83 pages.
Ioelovich and Figovsky, "Structure and Properties of Nanoparticles Used in Paper Compositions", Mechanics of Composite Materials, vol. 46, No. 4, 2010, pp. 435-442.
Ioelovich, Michael, "Cellulose as a Nanostructured Polymer: A Short Review." BioResources, vol. 3, No. 4, 2008, pp. 1403-1418.
Luukkanen, Lauri, "Reducing of Paper Porosity and Roughness Through Layered Structure", Aalto University School of Science and Technology, Master's thesis for the degree of Master of Science in Technology, Espoo, May, 2010, 132 pages.
Malaysian Examination Report dated Nov. 30, 2015 for Malaysian Patent Application No. PI 2011004631, 3 pages.
Malaysian Examination Report dated Oct. 15, 2015 for Malaysian Patent Application No. PI 2012004747, 3 pages.
Mathur, V. "GRI's Fibrous Filler Technology Presentation to TAPPI", Philadelphia, PA (slides only), 2005, pp. 1-10.
Mill (grinding) http://en_wikipedia.org/w/index.php?title-File:Hammer_mill_open-_front full.jgp, 8 pgs.
Mori, et al. "Effect of cellulose nano-fiber on calcium carbonate crystal form", Polymer Preprints, Japan, vol. 56, No. 2, 2007—1 page.
Morseburg, et al. "Assessing the combined benefits of clay and nanofibrillated cellulose in layered TMP-based sheets", Cellulose, No. 5, vol. 16, 2009, pp. 795-806.
Mullite, 2001 [downloaded online Dec. 6, 2016], Minerals Data Publishing.
Nakagaito, et al. "The effect of fiber content on the mechanical and thermal expansion properties of bio composites based on microfibrillated cellulose", Cellulose, vol. 15, 2008, pp. 459-494.
OPTIFINER™ DF Deflakers, "Improved quality through effective deflaking." Stock Preparation and Recycled Fiber Systems, Metso Paper, 2006, 4 pages.
Pinkney et al., "Microfibrillated Cellulose—A New Structural Material." Engineering Doctorate Conference (2012), Unviersity of Birminghamm 2 pgs.
Pohler et al. "Influence of fibrillation method on the character of nanofibrillated cellulose (NFC)." The Finnish Centre of Nanocellulosic Technologies, 22 pages.
Porubska, et al. "Homo- and heteroflocculation of papermaking fines and fillers", Colloids and Surfaces A: Physiochem. Eng. Aspects, Elsevier Science, vol. 210, 2002, pp. 223-230.
Subramanian, "Engineering Fine Paper by Utilizing the Structural Elements of the Raw Materials," TKK Reports in Department of Forest Products Technology, Series A1 Espoo 2008, pp. 1-66.
Product information for the Ultra-fine Friction Grinder "Supermasscolloider," 1 page, retrieved from http:www.masuko.com/English/product/Masscolloder.html (2014).
European Office Action dated Jun. 27, 2011 for European Application No. 09156683.6, 7 pages.
Russian Application No. 2011143854, (abstract) for EP No. 2236545A1.
Saito, et al. "Homogeneous Suspensions of Individualized Microfibrils from TEMPO-Catalyzed Oxidation of Native Cellulose," Biomacromolecules, American Chemical Society, vol. 7, No. 6, 2006, pp. 1687-1691.
Selder, et al. "Broke systems for LWC, MWC and HWC Papers", Voith Sulzer Paper Technology, 7 pages.
Silenius, Petri, "Improving the Combinations of Critical Properties and Process Parameters of Printing and Writing Papers and Paperboards by New Paper-Filling Methods", Helsinki University of Technology Laboratory of Paper Technology Reports, Series A 14, Espoo 2002, 168 pages.
Sinnott et al. "Slurry Flow in a Tower Mill", Seventh International Conference on CFO in the Minerals and Process Industries, CSIRO, Melbourne, Australia, Dec. 9-11, 2009, pp. 1-7.
Taiwan Examination and Search Report dated Apr. 29, 2016 for Taiwan Patent Application No. 100114616, 11 pages.
Yano, Hiroyuki, High Performance of Bio Fibers by the Addition of Filler, vol. 55, Machine No. 4, 2009, pp. 63-68.
Canadian Office Action for Canadian Patent Application No. 2755495 dated May 11, 2015, 4 pages.
Chinese Office Action for Chinese Patent Application No. 201080015262.5 dated Jul. 9, 2013, 6 pages.
Notice of Opposition to European Patent No. 2236545 dated May 27, 2015, 19 pages.
Korean Office Action and Notice Requesting Consultation, dated Nov. 25, 2016 for Korean Patent Application No. 10-2011-7025315, 10 pages.
Abe, et al. "Obtaining Cellulose Nanofibers with a Uniform Width of 15 nm from Wood", Bio macromolecules, vol. 8, (2007) pp. 3276-3278.
Ahola, Susanna, "Properties and Interfacial Behavior of Cellulose Nano fibrils." Doctoral Thesis, 2008, 82 pages.
Ankerfors, et al. "Nano Cellulose Developments in Scandinavia", Paper and Coating Chemistry Symposium (PCCS), Jun. 2009, Hamilton, Canada, 43 pages.
Ankerfors, Mikael, "The manufacture of micro fibrillated cellulose (MFG) its applications." Nanostructured cellulose and new cellulose derivatives seminar, Nov. 2006, pp. 1-40.
Atrex G-Series, Megatrex, "Technology for Reject Treatment and Recovery." 2 pages.

(56) References Cited

OTHER PUBLICATIONS

Australian Patent Examination Report No. 1 dated Feb. 26, 2014 for Australian Patent Application No. 2013202515, 3 pages.
Australian Patent Examination Report dated Jul. 26, 2012 for Australian Patent Application No. 2010247184, 6 pages.
Australian Patent Examination Report No. 1 dated May 14, 2013 for Australian Patent Application No. 2011246521, 2 pages.
Australian Patent Examination Report No. 1, dated Sep. 16, 2015 for Australian Patent Application No. 2014227494, 3 pages.
Australian Examination Report dated May 3, 2013 for Australian Patent Application No. 2011246522, 4 pages.
Berglund et al., "Nanostructured Cellulose Products." Finnish-Swedish Wood Material Science Research Programme Opening Seminar, 2004, Helsinki, Finland, 28 pages.
Bhatnagar et al., "Processing of Cellulose Nanofiber-reinforced Composites." Journal of Reinforced Plastics and Composites, vol. 24, No. 12, 2005, pp. 1259-1268.
Canadian Office Action dated Apr. 28, 2016 for Canadian Patent Application No. 2,796,132, 3 pages.
Canadian Office Action dated May 11, 2015 for Canadian Patent Application No. 2,755,495, 4 pages.
Canadian Office Action dated Sep. 2, 2015 for Canadian Patent Application No. 2,796,132, 3 pages.
Canadian Office Action dated Jan. 7, 2014 for Canadian Application No. 2,755,495, 5 pages.
Canadian Office Action dated Dec. 18, 2013 for Canadian Application No. 2,748,137, 2 pages.
Canadian Office Action dated Apr. 26, 2016 for Canadian Patent Application No. 2, 796, 135, 4 pages.
Canadian Office Action dated Sep. 3, 2015 for Canadian Patent Application No. 2, 796, 135, 3 pages.
Characterisation Newsletter "Micro fibrillated Cellulose", No. 5, Jan. 2009, pp. 1-2.
Chinga-Carrasco, "Cellulose fibres, nanofibrils and microfibrils: The morphological sequence of MFC components from a plant physiology and fibre technology point of view." Chinga-Carrasco Nanoscale Research Letters 2011, vol. 6:417, 8 pages.
Chinese Fifth Office Action dated Feb. 15, 2016 for Chinese Patent Application No. 201080015263.X, 7 pages.
Chinese First Notification of Office Action for Chinese Patent Application No. 201510628033.5, dated Jan. 10, 2017, 17 pages.
Chinese First Office Action dated May 6, 2014 for Chinese Patent Application No. 201180020949.2, 14 pages.
Chinese First Office Action dated Oct. 23, 2013 for Chinese Patent Application No. 201080015263.X, 22 pages.
Chinese Fourth Office Action dated Oct. 13, 2015 for Chinese Patent Application No. 201080015263.X, 10 pages.
Chinese Office Action dated Jan. 6, 2014 for Chinese Application No. 201080003690.6, 15 pages.
Chinese Second Office Action dated Jun. 11, 2014 for Chinese Patent Application No. 201080015263.X, 14 pages.
Chinese Second Office Action dated Mar. 4, 2015 for Chinese Patent Application No. 201180020949.2, 5 pages.
Chinese Third Office Action dated Feb. 27, 2015 for Chinese Patent Application No. 201080015263.X, 23 pages.
Chinese Office Action dated Apr. 10, 2015 for Chinese Patent Application No. 201180020953.9, 5 pages.
Chinese Office Action dated Jan. 13, 2015 for Chinese Patent Application No. 201180020953.9, 12 pages.
Chinese Office Action dated May 22, 2014 for Chinese Patent Application No. 201180020953.9, 20 pages.
Chinga-Carrasco, et al. "Computer-assisted quantification of the Iti-scale structure of films made of nanofibrillate cellulose." J. Nanopart Res. 2010, pp. 841-851.
Peng et al., "Drying cellulose nanofibrils: in search of a suitable method." Published online: Dec. 2, 2011, Cellulose, DOI 10.1007/s10570-011-9630-z, 12 pages.
De Oliveira et al., "Synthesis and Characterization of Microcrystalline Cellulose Produced from Bacterial Cellulose," J. Therm. Anal. Caiorim, (2011) 106, pp. 703-709.

European Communication dated Aug. 6, 2013 for European Patent Application No. 11716257.8, 4 pages.
Eichhorn et al., "Review: current international research into cellulose nanofibres and nanocomposites." Journal of Materials Science, vol. 45, No. 1, 2010, pp. 1-33.
Eriksen et al., "The use of microfibrillated cellulose produced from kraft pulp as strength enhancer in TMP paper." Nordic Pulp and Paper Research Journal, vol. W. No. 3, 2008, p. 299-304.
European Office Action of Mar. 10, 2017 for European Patent Application No. 10 713 884.4, 4 pages.
Response to the Communication dated Nov. 5, 2013 for European Patent Application No. 11716257.8, 11 pages.
European Communication dated May 2, 2016 for European Patent Application No. 10 713 884.4, 3 pages.
European Examination Report dated Oct. 27, 2015 for European Patent Application No. 14 175 471.3, 3 pages.
European Examination Report dated Oct. 27, 2015 for European Patent Application No. 14 175 451.5, 3 pages.
European Examination Report dated Sep. 16, 2016 for European Patent Application No. 14 175 471.3, 4 pages.
European Extended European Search Report dated Jan. 15, 2013, for European Patent Application No. 12189681.5, 5 pages.
European Communication dated Sep. 24, 2012 for European Patent Application No. 10711423.3, 10 pages.
The Office Action dated Jan. 27, 2014 for U.S. Appl. No. 13/138,646, 14 pages.
The Office Action dated Jan. 28, 2014 for U.S. Appl. No. 13/138,647, 18 pages.
Habibi et al., "Cellulose Nanocrystals: Chemistry, Self-Assembly, and Applications," Chem. Rev. (2010) 110, pp. 3479-3500.
Lavoine et al., "Microfibrillated Cellulose—Its Barrier Properties and Applications in Cellulosic Materials: A Review," Carbohydrate Polymers 90 (2012) pp. 735-764.
Samir et al., "Review of Recent Research into Cellulosic Whiskers, Their Properties and Their Application in Nanocomposite Field," Biomacromolecules (2005) 6, pp. 612-626.
Siqueira et al., "Cellulosic Bionanocomposites: A Review of Preparation, Properties and Applications," Polymers (2010) 2, pp. 728-765, doi: 10.3390/polym2040728.
Japanese Office Action dated Nov. 7, 2017 for Japanese Patent Application No. 2016-234040, 11 pages.
Subramanian et al., "Calcium Carbonate—Cellulose Fibre Composites; the Role of Pulp Refining," Paper Technology, Dec. 2006 Pulp Refining, pp. 27-31.
Falini et al., "Oriented Crystallization of Vaterite in Collagenous Matrices," Chem. Eur. J. (1998) 4:1048-1052.
Champinhos Jr. "Sustainable Plantations of High-Yield Eucalyptus Trees of Production of Fiber: the Aracruz Case." New Forests (1999) 17: 129-143.
Auad et al., "Charactizeration of Nanocellulose-Reinforced Shape Memory Polyurethanes." Polymer International (2008) 57: 651-659. Online Publication Date: Dec. 13, 2007.
Kenny et al., "Lime and Limestone," Ulmann's Encyclopedia of Industrial Chemistry (2012) 21: 37-69.
Third Party Observations dated Jun. 6, 2012 for European Patent Application No. 09156683.6, 4 pages.
Third Party Observations dated Oct. 21, 2011 for European Patent Application No. 09156683.6, 4 pages.
Third Party Observations dated Jun. 6, 2012 for European Patent Application No. 09156703.2, 4 pages.
Third Party Observations dated May 18, 2011 for European Patent Application No. 09156703.2, 6 pages.
Third Party Observations dated Apr. 19, 2013 for European Patent Application No. 10161173.9, 5 pages.
Third Party Observations dated May 27, 2011 for European Patent Application No. 09156683.6, 7 pages.
European Office Action dated Feb. 6, 2014 for related European Application No. 12 189 687.5-1308, 3 pages.
European Office Action dated Mar. 7, 2014, for European Application No. 10 727 476.3-1308, 5 pages.
European Office Action dated May 26, 2014, for European Application No. 10 727 476.3-1308, 4 pages.

(56) References Cited

OTHER PUBLICATIONS

European Office Action dated Nov. 30, 2012 for European Application No. 10 727 476.3-2124, 4 pages.
European Office Action dated Oct. 25, 2013 for European Application No. 10 727 476.3-1308, 3 pages.
European Office Action dated May 2, 2016 for European Patent Application No. 10 713 884.4, 3 pages.
European Partial European Search Report of European Application No. 16163032, dated Jul. 26, 2016, 3 pages.
European Search Report dated Jun. 26, 2009 for European Application No. 09156703.2, 7 pages.
European Search Report dated Sep. 8, 2010 for European Application No. 10161166.3.
European Office Action dated Mar. 29, 2016 for European Patent Application No. 11719499.3, 3 pages.
European Third Party Observation dated Jun. 11, 2012 for European Application No. 10161173.9.
European Third Party Observation dated Jun. 6, 2012 for European Application No. 09156703.2, 4 pages.
International Preliminary Report on Patentability dated Oct. 30, 2012 for PCT/EP2011/056542, 6 pages.
European Third Party Observations dated Apr. 12, 2013 for European Application No. EP 10161173.9, 4 pages.
European Third Party Observations dated Feb. 17, 2012 for European Application No. EP 10713884.4, 6 pages.
European Third Party Observations dated Feb. 4, 2013 for European Application No. EP 11719499.3, 8 pages.
Iwamoto, et al. "Nano-fibrillation of pulp fibers for the processing of transparent nanocomposites", Applied Physics A, vol. 89, 2007, pp. 461-466.
European Third Party Observations dated May 18, 2011 for European Application No. 09156683.6, 6 pages.
European Third Party Observations dated Oct. 21, 2011 for European Application No. 091566683.6, 4 pages.
European Third Party Observations pursuant to Article 115(1)EPC concerning European Patent Application No. 12 189 581.5, dated Jul. 10, 2014, 15 pages.
European Third Party Observations pursuant to Article 115(1)EPC concerning European Patent Application No. 10727476.3, dated Jul. 22, 2014, 18 pgs.
European Office Action from the European Patent Office dated Mar. 15, 2013 for European Patent Application No. 10 161 166.3, 4 pages.
Innventia, "Processes for Nano cellulose," http://www.innventia.com/templates/STFIPage_ 9108.aspx, 2011, 1 page.
European Office Action from the European Patent Office dated Oct. 11, 2013 for European Patent Application No. 11 719 499.3, 4 pages.
International Search Report and Written Opinion for International Application No. PCT/EP2010/054231, dated Jun. 7, 2010, 12 pages.
Fukui, Yoshitaka, "Microfibrillated Cellulose", vol. 60, No. 24, 1985, pp. 5-12.
GL&V, The Atrex System at M-real Hallein Paper Mill in Austria, "Atrex is running well and us money!" 4 pages.
Henriksson, "Cellulose Nanofibril Networks and Composites", KTH Chemical Science and Engineering, 2008, 60 pages.
Hentze, Hans-Peter, "From Nano cellulose Science towards Applications", VTT—Technical Research Center of Finland, PulpPaper 2010, Jun. 2010, Helsinki, pp. 1-24.
International Search Report and Written Opinion dated Jun. 22, 2011 for International Application No. PCT/EP2011/056540, 11 pages.
http://puu.tkk.fl/em/research/research_groups/chemical_pupling_and_wood_refinery/seminar_presentations/knuts_100609_laitoksen_sisainen_seminaariesitys.pdf;Knuts, M. SC. Aaro, "Process installation and optimization to refine and produce NFC materials." pp. 1-9.
India, Examination Report dated Jun. 12, 2017 for Indian Patent Application No. 1474/MUMNP/2011.

Indonesian Examination Report dated Oct. 13, 2015 for Indonesian Patent Application No. W00201103474, 4 pages.
Indonesian Office Action dated Mar. 10, 2016 for Indonesian Patent Application No. W00201103469, 2 pages.
Indonesian Office Action dated Apr. 18, 2017 for Indonesian Patent Application No. WO 00 2012 04369, 4 pages.
Klemm et al., "Cellulose: Fascinating Biopolymer and Sustainable Raw Material." Angew Chem. Int Ed. 2005 vol. 44, pp. 3358-3393.
Peltola, Maarit, "Preparation of Microfibrillated Cellulose" Master of Science Thesis, Tampere University of Technology, May, 2009, 98 pages.
Henriksson, et al. "Cellulose Nanopaper Structures of High Toughness", Biomacromolecules, vol. 9, 2008, pp. 1579-1585.
Notice of Opposition against EP 2236664 B1, EP Application No. 09156683.6, dated Sep. 29, 2016 from European Patent Office.
European Office Action dated Sep. 20, 2016 for European Patent Application No. 14 175 451.5, 3 pages.
Third Party Observations dated Mar. 16, 2015 for European Patent Application No. 14 175 451.5.
European Search Report dated Oct. 23, 2014 for European Patent Application No. 14 175 451.5, 6 pages.
Campinhos Jr. "Sustainable Plantations of High-Yield Eucalyptus Trees of Production of Fiber: the Aracruz Case." New Forests (1999) 17: 129-143.
European Notice of Opposition dated Dec. 19, 2014 for European Patent No. EP2386682, 17 pages.
European Search Search Report dated Jun. 26, 2009 for European Application No. EP 09156683.6, 9 pages.
European Third Party Observations dated Apr. 12, 2013 for European Application No. EP 10161166.3, 4 pages.
European Third Party Observations dated Feb. 4, 2013 for European Application No. EP 11716257.8, 8 pages.
European Third Party Observations dated Jan. 9, 2012 for European Application No. EP 10161166.3, 6 pages.
Europe, Third Party Observations dated Jan. 9, 2012 for European Application No. EP 10161173.9, 6 pages.
European Third Party Observations dated Oct. 21, 2011 for European Application No. EP 09156703.2, 4 pages.
Japanese Office Action dated Apr. 14, 2015 for Japanese Patent Application No. 2012-502647, 7 pages.
Europe, Office Action dated Mar. 15, 2013 for European Application No. 10161166.3, 4 pages.
Notice of Opposition against EP 2236664 B1, EP Application No. 09156683.6, dated Jul. 18, 2017 from European Patent Office, 10 pages.
Japanese Office Action dated Mar. 31, 2015 for Japanese Patent Application No. 2013-506621, 7 pages.
Korean Office Action dated Aug. 11, 2017 for Korean Patent Application No. 10-2017-7017876, 5 pages.
OPTIFINER™ DF Deflakers, "Improved quality through effective deflaking." Stock Preparation and Recycled Fiber Systems, Metso Paper, 4 pages.
Indian Examination Report dated Aug. 24, 2017 for Indian Patent Application No. 2046/MUMNP/2011, 7 pages.
Somboon, et al. "Grit segments in TMP refining. Part 2: Potential for energy reduction", Appita Journal, vol. 62, No. 1, 2009, pp. 42-45 and 59.
Smook, Handbook for Pulp and Paper Technologies, 1992, Angus Wilde Publications, 2nd Edition, Chap. 13.
Somboon, et al. "Grit segments in TMP refining. Part 1: Operating parameters and pulp quality", Appita Journal, vol. 62 No. 1, 2009, pp. 37-41.
Somboon, Phichit, "On the Application of Grits to Therrnomechanical Pulp Refining." TKK Reports in Forest Products Technology, Series A7, Espoo 2009, 61 pages.
Spence, et al. "The effect of chemical composition on microfibrillar cellulose films from wood pulps: Mechanical processing and and physical properties", BioResource Technology, vol. 101, 2010, pp. 5961-5968.
Syverud, et al. "The influence of microfibrillated cellulose, MFG, on paper strength and surface properties", Paper and Fibre Research Institute and Norwegian University of Science and Technology, pp. 1-32.

(56) References Cited

OTHER PUBLICATIONS

Taiwan Examination and Search Report dated May 17, 2016 for Taiwan Patent Application No. 100114616, 11 pages.
Taiwan Examination Report dated Feb. 11, 2014 for Taiwanese Application No. 099109562, 17 pages.
Taniguchi, Takashi, "New Films Produced from Microfibrillated Natural Fibres", Polymer International, vol. 47, 1998, pp. 291-294.
Terao, et al. "Pulp-Filler Interaction (3)—The Influence of Wet Pressing and Cellulosic Fines Addition on the Structure and Properties of Filler Loaded Papers", vol. 8, 1989, pp. 65-73.
Torvinen, et al. "Flexible filler—nanocellulose structures", VTT Technical Research Centre of Finland—1 page.
UK Search Report for UK Application No. GB0908401.3, dated Sep. 14, 2009, 1 page.
Vietnam, First Examination Report dated Dec. 30, 2014 for Vietnamese Patent Application No. 1-2012-03429, 4 pages.
Vietnam, Second Examination Report dated Oct. 8, 2015 for Vietnamese Patent Application No. 1-2012-03429, 5 pages.
Vietnam, Third Examination Report dated Apr. 28, 2016 for Vietnamese Patent Application No. 1-2012-03429, 2 pages.
Waterhouse, J .F., "Whither Refining?", Institute of Paper Science and Technology, No. 649, 1997, 40 pages.
Zhao, et al., "Ultrasonic technique for extracting nanofibers from nature materials" Applied Physics Letters 90, 073112, 2007, 2 pages.
Zirconium Oxide Data sheet, downloaded online from www.stanfordmaterials.com, downloaded on Jan. 12, 2012, 7 pages.
Zirconium, Silicate Data sheet, downloaded online from www.reade.com, downloaded on Jan. 12, 2012, 2 pages.
Zou, et al. "Production of Nanocrystalline Cellulose and its Potential Applications in Specialty Papers." Pira Specialty Papers Conference, Nov. 2010, pp. 1-30.
Zou, et al. "Review of Microfibrillated Cellulose (MFG) for Papermaking", Pulp and Paper Engineering, School of Chemical and Biomolecular Eng., Georgia Institute of Technology, 10 pages.
Korean Office Action dated Jul. 28, 2016 for Korean Patent Application No. 10-2011-7025315, 7 pages.
Russian Office Action dated Jan. 21, 2014 for Russian Patent Application No. 2011143854, 7 pages.
Taiwan Reasons for Rejection dated Nov. 7, 2014 for Taiwanese Application No. 099109562, 7 pages.
Taiwan Reasons for Rejection dated Apr. 26, 2017 for Taiwanese Application No. 099109562, 5 pages.
Ahola et al., "Model Films from Native Cellulose Nanofibrils. Preparation, Swelling, and Surface Interactions," Biomacromolecules, 9: 2008 pp. 1273-1282.
Canadian Office Action for Canadian Patent Application No. 2755493, dated Feb. 19, 2015, 3 pages.
Canadian Office Action for Canadian Patent Application No. 2755493, dated May 28, 2014, 4 pages.
U.S. Non-Final Office Action dated Mar. 19, 2018 for U.S. Appl. No. 14/474,705, 8 pages.
Chinese Office Action for corresponding Chinese Patent Application No. 201610882363.1, dated Jan. 25, 2018, 27 pages.
European Search Report for European Patent Application No. 17190151.5, dated Mar. 19, 2018, 5 pages.
European Office Action for European Patent Application No. 10713884.4, dated Apr. 19, 2018, 4 pages.
Crofton et al., " Dielectric Studies of Cellulose and Its Derivatives: 1. Acetylation of Cellulose," Polymer (1982) 23:1605-1608.
Decision Revoking European Patent No. 2236664 dated Nov. 2, 2017, 12 pages.
Esau, Katherine, "Chapter 4, Cell Wall," Anatomy of Seed Plants, 2nd Edition, (1977) pp. 43-48.
European Extended Search Report for European Patent Application No. 14175471.3 dated Oct. 23, 2014, 8 pages.
European Office Action for corresponding European Patent Application No. 14175471.3 dated Oct. 6, 2017, 3 pages.

European Third Party Observations pursuant to Article 115(1)EPC concerning European Patent Application No. 12 189 681.5, dated Jul. 10, 2014, 15 pages.
European Communication from the Europeanan Patent Office dated Aug. 6, 2013 for European Patent Application No. 11716257.8, 4 pages.
Extended European Search Search Report dated Jun. 26, 2009 for European Application No. Ep 09156683.6, 9 pages.
Fahn, A., "Plant Anatomy Fourth Edition," (1990) pp. 32-39.
Fengel et al., "Chapter 4. Cellulose," Wood Chemistry, Ultrastructure, Reactions, (1983) pp. 66-105.
Fengel, D., "Ideas on the Ultrastructure Organization of the Cell Wall Components," J. Polymer Sci.: Part C, No. 36 (1971) pp. 383-392.
Frey-Wyssling and Mühlethaler, "The Fine Structure of Cellulose." Fortschritte der Chemie Organischer Naturstoffe (1951) pp. 1-27.
Hamann, Lutzm Papiertechnische Stiftung, SUNPAP Workshop May 10, 2011, Seventh Framework Programme, 24 pages.
Herrick et al. "Microfibrillated Cellulose: Morphology and Accessibility," Journal of Applied Polymer Science, Applied Polymer Symposium 37—Proceedings of the Ninth Cellulose Conference II. Symposium on Cellulose and Wood as Future Chemical Feedstocks and Sources of Energy, and General Papers, John Wiley & Sons, Inc., May 24-27, 1982, 11 pages.
http://puu.tkk.fi/em/research/research_groups/chemical_pupling_and_wood_refinery/seminar_presentations/43knuts_100609_laitoksen_sisainen_seminaariesitys.pdf;Knuts, M.SC. Aaro, ""Process installation and optimization to D refine and produce NFC materials."" pp. 1-9, 2010.
Hult et al., "Cellulose Fibril Aggregation—An Inherent Property of Kraft Pulps," Polymer 42 (2001) pp. 3309-3314.
International Search Report and Written Opinion for International Application No. PCT/EP2011/056540, dated Jun. 22, 2011, 10 pages.
International Search Report and Written Opinion for International Application No. PCT/EP2011/056542, dated May 27, 2011, 9 pages.
International Search Report and Written Opinion dated Sep. 3, 2010 for International Application No. PCT/EP2010/054233, 12 pages.
Iwamoto, et al. "Optically transparent composites reinforced with plant fiber-based nanofibers", Applied Physics A, vol. 81, 2005, pp. 1109-1112.
Japanese Office Action for corresponding Japanese Patent Application No. 2014-248634 dated Jan. 9, 2018, 11 pages.
Japanese Office Action for corresponding Japanese Patent Application No. 2014-248634 dated Mar. 10, 2017, 6 pages.
Korean Office Action for Korean Patent Application No. 10-2017-7011268 dated Jun. 21, 2017, 5 pages.
Malaysian Substantive Examination Report for Malaysian Patent Application No. PI 2014002508 dated Nov. 30, 2017, 4 pages.
McGinnis and Shafizadeh, "Chapter 1 Cellulose and Hemicellulose," Pulp and Paper: Chemistry and Chemical Technology, (1980) pp. 1-38.
McGraw-Hill, "Cell Walls (Plant)," Encyclopedia of Science and Technology, 5th edition, (1982), pp. 737-741.
Notice of Appeal filed Dec. 21, 2017 for corresponding European Patent No. EP2236664, 1 page.
Patt et al., "Paper and Pulp," Ulmann's Encyclopedia of Industrial Chemistry, published online Jun. 2000, 157 pages.
International Preliminary Report on Patentability and the Written Opinion dated Oct. 4, 2011 from PCT Patent Application No. PCT/EP2010/054231, 8 pages.
International Search Report and Written Opinion dated Aug. 17, 2010 for PCT Application No. PCT/EP2010/054233, 12 pages.
International Search Report and Written Opinion dated Jun. 22, 2011 for PCT Application No. PCT/EP2011/056540, 11 pages.
International Search Report and Written Opinion dated May 27, 2011 for PCT Application No. PCT/EP2011/056542, 9 pages.
International Search Report and Written Opinion of the International Searching Authority dated Jun. 7, 2010 for PCT Application No. PCT/EP2010/054231, 12 pages.
Pöhler, Tiina & Lappalainen, Timo & Tammelin, Tekla & Eronen, Paula & Hiekkataipale, Panu & Vehniäinen, Annikki & M. Koskinen,

(56) References Cited

OTHER PUBLICATIONS

Timo. (2011). "Influence of fibrillation method on the character of nanofibrillated cellulose (NFC)," 2010 TAPPI International Conference on Nanotechnology for the Forest Product Industry, Dipoli Congress Centre, Espoo, Finland, Sep. 27-29, 2010, 22 pages.
Provision of the minutes in accordance with Rule 124(4) EPC dated Nov. 2, 2017, of the oral for proceedings corresponding European Patent No. EP2236664, 5 pages.
Ragnar et al., "Pulp," Ullmann's Encylopedia of Industrial Chemistry, published on-line 2000, 89 pages.
Response to Notice of Opposition Against EP2236664, dated Mar. 2, 2017, submitted to the European Patent Office, 9 pages.
Roberts, J.C., "Chapter 2, The Material of Paper," The Chemistry of Paper, RSC Paperbacks, 1996, pp. 11-25.
Roberts, J.C., "Chapter 4, The Material of Paper," The Chemistry of Paper, RSC Paperbacks, 1996, pp. 52-68.
Rowland and Roberts, "The Nature of Accessible Surfaces in the Microstructure of Cotton Cellulose," Journal of Polymer Science: Part A-1, vol. 10, (1972) pp. 2447-2461.
Russian Office Action from Russian Patent Application No. 2011143854 filed on Mar. 10, 2010, 3 pages.
Russian Official Action dated Apr. 22, 2015 for Russian Patent Application No. 2015109771, 4 pages.
Saito et al., "Cellulose Nanofibers Prepared by TEMPO-Mediated Oxidation of Native Cellulose," Biomacromolecules, (2007) 8:2485-2491.
Selder, H.; Mannes, W., and Matzke, W., "Broke systems for LWC, MWC and HWC Papers", Voith Sulzer Paper Technology, 8 pages, Dec. 2011.
Sixta "Handbook of Pulp." Wood Structure and Morphology (2006), vol. 1, 41-42.
Statement of Grounds of Appeal for European Patent No. 2236664 dated Mar. 12, 2018, 13 pages.
Summons to Attend Oral Proceedings Pursuant to Rule 115(1) EPC dated Mar. 22, 2017 for corresponding European Patent No. EP2236664, 10 pages.
Syverud and Stenius, "Strength and Barrier Properties of MFC Films," Cellulose 16:75-85 (2009).
Taiwan Examination Report and Search Report for Taiwan Patent Application No. 099109560 dated Jun. 22, 2015, 12 pages.
Taiwan, Office Action for related Taiwanese Application No. 099115704, dated Jul. 14, 2014.
Third Party Observations dated Mar. 16, 2015 for European Patent Application No. 14175471.3, 6 pages.
Third Party Written Submission dated Sep. 25, 2017 for corresponding European Patent No. 2236664, 2 pages.
"Paper Coating Pigments," TAPPI Monograph Series No. 30, 1966, pp. 34-35.
U.S. Office Action dated Nov. 18, 2015 for U.S. Appl. No. 13/640,513.
U.S. Office Action dated Jan. 27, 2014 for U.S. Appl. No. 13/138,646, 14 pages.
U.S. Office Action dated Jan. 28, 2014 for U.S. Appl. No. 13/138,647, 18 pages.
Non-Final Office Action dated Nov. 10, 2014 for U.S. Appl. No. 13/640,513, 12 pages.
U.S. Final Office Action dated Aug. 4, 2017 for U.S. Appl. No. 14/474,705, 14 pages.
U.S. Final Office Action dated Jan. 12, 2017 for U.S. Appl. No. 13/640,513, 10 pages.
U.S. Final Office Action dated Mar. 26, 2014 for U.S. Appl. No. 13/640,513, 14 pages.
U.S. Final Office Action dated May 6, 2016 for U.S. Appl. No. 14/474,705, 11 pages.
U.S. Final Office Action dated May 9, 2013 for U.S. Appl. No. 13/138,647, 15 pages.
U.S. Final Office Action dated Nov. 18, 2015 for U.S. Appl. No. 13/640,513, 8 pages.
U.S. Issue Fee Payment dated Sep. 11, 2014 for U.S. Appl. No. 13/138,647, 5 pages.
U.S. Issue Notification dated Oct. 28, 2014 for U.S. Appl. No. 13/138,647, 1 page.
U.S. Non-Final Office Action dated Dec. 28, 2017 for U.S. Appl. No. 13/640,513, 9 pages.
U.S. Non-Final Office Action dated Dec. 3, 2015 for U.S. Appl. No. 14/474,705, 13 pages.
U.S. Non-Final Office Action dated Feb. 10, 2017 for U.S. Appl. No. 14/474,705, 15 pages.
U.S. Non-Final Office Action dated Jan. 22, 2013 for U.S. Appl. No. 13/138,647, 19 pages.
U.S. Non-Final Office Action dated Mar. 11, 2016 for U.S. Appl. No. 13/640,513, 8 pages.
U.S. Non-Final Office Action dated May 15, 2015 for U.S. Appl. No. 13/640,513, 13 pages.
U.S. Non-Final Office Action dated Sep. 11, 2013 for U.S. Appl. No. 13/138,647, 17 pages.
U.S. Non-Final Office Action dated Sep. 6, 2013 for U.S. Appl. No. 13/640,513, 13 pages.
U.S. Notice of Allowance dated May 23, 2014 for U.S. Appl. No. 13/138,647, 8 pages.
U.S. Notice of Allowance dated Sep. 5, 2014 for U.S. Appl. No. 13/138,647, 7 pages.
U.S. Notice of Allowance dated Dec. 22, 2017 for U.S. Appl. No. 14/808,480, 8 pages.
U.S. Non-Final Office Action dated May 19, 2017 for U.S. Appl. No. 14/808,480, 6 pages.
U.S. Final Office Action dated Nov. 28, 2016 for U.S. Appl. No. 14/808,480, 8 pages.
U.S. Non-Final Office Action dated May 2, 2016 for U.S. Appl. No. 14/808,480, 15 pages.
U.S. Non-Final Office Action dated Oct. 21, 2015 for U.S. Appl. No. 14/808,480, 11 pages.
U.S. Notice of Allowance dated Dec. 21, 2017 for U.S. Appl. No. 13/640,533, 7 pages.
U.S. Non-Final Office Action dated Sep. 1, 2017 for U.S. Appl. No. 13/640,533, 8 pages.
U.S. Notice of Allowance dated May 22, 2017 for U.S. Appl. No. 13/640,533, 6 pages.
U.S. Final Office Action dated Nov. 28, 2016 for U.S. Appl. No. 13/640,533, 8 pages.
U.S. Non-Final Office Action dated Mar. 24, 2016 for U.S. Appl. No. 13/640,533, 12 pages.
U.S. Notice of Allowance dated Nov. 25, 2015 for U.S. Appl. No. 13/640,533, 8 pages.
U.S. Notice of Allowance dated Aug. 20, 2015 for U.S. Appl. No. 13/640,533, 6 pages.
U.S. Notice of Allowance dated Jan. 20, 2015 for U.S. Appl. No. 13/640,533, 5 pages.
U.S. Notice of Allowance dated Dec. 2, 2014 for U.S. Appl. No. 13/640,533, 8 pages.
U.S. Non-Final Office Action dated Apr. 25, 2014 for U.S. Appl. No. 13/640,533, 15 pages.
U.S. Final Office Action dated Dec. 19, 2014 for U.S. Appl. No. 13/640,533, 8 pages.
U.S. Non-Final Office Action dated Jun. 14, 2013 for U.S. Appl. No. 13/640,533, 15 pages.
European Third Party Observation dated Jan. 9, 2012 for European Patent Application No. 10161173.9.
Taiwanese Office Action and Search Report for Taiwanese Patent Application No. 104124236 dated Feb. 26, 2018, 10 pages.
European Notice of Opposition dated Dec. 19, 2014 for European Patent No. EP2386683, 15 pages.
European Search Report for European Patent Application No. 17188196.4, dated Nov. 17, 2017, 6 pages.
Indonesian Office Action dated Feb. 13, 2018 for Indonesian Patent Application No. W00201204368, 4 pages.
New Zealand Office Action for New Zealand Patent Application No. 603756 dated Jun. 20, 2013, 2 pages.
Russian Office Action dated Apr. 22, 2015 for Russian Patent Application No. 2012150441, 7 pages.
Singapore Office Action for Singapore Patent Application No. 2012075610, dated Dec. 31, 2014, 21 pages.

(56) References Cited

OTHER PUBLICATIONS

Singapore Search and Examination Report for Singapore Patent Application No. 2012075610, dated Nov. 4, 2015, 16 pages.
Taiwan Office Action for Taiwanese Application No. 1-2012-03429, dated Dec. 30, 2014, 4 pages.
Taiwan Office Action for Taiwanese Application No. 1-2012-03429, dated Oct. 8, 2015, 3 pages.
Taiwan Office Action for Taiwanese Application No. 1-2012-03429, dated Apr. 28, 2016, 2 pages.
International Report on Patentability for International Patent Application No. PCT/EP2010/054233, dated Oct. 2, 2011, 9 pages.
International Report on Patentability for International Patent Application No. PCT/EP2011/056540, dated Oct. 30, 2012, 6 pages.
Brazilian Examination Report for Brazilian Patent Application No. PI1013180-9, dated Oct. 16, 2018, 6 pages.
Chinese Second Office Action dated Sep. 12, 2018 for Chinese Patent Application No. 201610882363.1, 6 pages.
Daiyong et al., "Advances in Cellulose Chemistry," J. of Chemical Industry and Engineering, vol. 57, No. 8, (2006), pp. 1782-1791.
Daiyong, Ye, "Preparation of Nanocellulose," Progress in Chemistry, vol. 19, No. 10, (2007), pp. 1568-1575.
European Office Action for corresponding European Patent Application No. 14175471.3 dated May 17, 2018, 3 pages.
European Search Report for European Patent Application No. 18152927.2, dated May 7, 2018, 6 pages.
Indian Examination Report dated Jun. 5, 2018 for Indian Patent Application No. 2018/MUMNP/2011, 6 pages.
Indian Examination Report dated Jun. 12, 2018 for Indian Patent Application No. 2404/MUMNP/2012, 6 pages.
Indian Examination Report dated Jun. 29, 2018 for Indian Patent Application No. 2424/MUMNP/2012, 5 pages.
Japanese Official Action dated May 22, 2018 for Japanese Patent Application No. 2016-234040, 4 pages.
Ling-ling and Xiao-quan, "Research Status of the Nano-Crystalline Cellulose," J. of Cellulose Science and Technology, vol. 16, No. 2, (2008), pp. 73-78.
"Packaging Technical Manual," Edited by Japan Packaging Technology Association (1994), 12 pages.
Response by Opponent to Notice of Appeal Against EP2236664, dated Jul. 3, 2018, submitted to the European Patent Office, 15 pages.
Opponent Submission Preparation Oral Proceedings Against EP2236664, dated Nov. 13, 2018, 5 pages.
Russian Search Report dated Apr. 25, 2018 for Russian Patent Application No. 2014130594, 4 pages.
U.S. Final Office Action for U.S. Appl. No. 14/474,705, dated Sep. 27, 2018, 9 pages.
U.S. Final Office Action for U.S. Appl. No. 13/640,513, dated Oct. 10, 2018, 9 pages.
U.S. Non-Final Office Action for U.S. Appl. No. 16/040,652, dated Nov. 13, 2018, 15 pages.
U.S. Notice of Allowance dated May 11, 2018 for U.S. Appl. No. 13/640,533, 7 pages.
U.S. Notice of Allowance dated Apr. 24, 2018 for U.S. Appl. No. 14/808,480, 8 pages.
European Office Action for European Patent Application No. 14175471.3, dated Oct. 15, 2018, 4 pages.

* cited by examiner

PROCESS FOR THE PRODUCTION OF NANO-FIBRILLAR CELLULOSE GELS

CROSS-REFERENCE TO RELATED APPLICATIONS

This is a continuation of U.S. application Ser. No. 13/138,646, filed Oct. 14, 2011, now U.S. Pat. No. 8,871,056, which is a U.S. national phase of PCT Application No. PCT/EP2010/054233, filed Mar. 30, 2010, which claims priority to European Application No. EP 09156703.2, filed Mar. 30, 2009 and U.S. Provisional Application No. 61/212,073, filed Apr. 6, 2009, the contents of which are hereby incorporated by reference.

The present invention relates to a process for producing nano-fibrillar cellulose gels and the nano-fibrillar cellulose gels obtained by this process.

Cellulose is the structural component of the primary cell wall of green plants and is the most common organic compound on Earth. It is of high interest in many applications and industries.

Cellulose is the major constituent of paper and cardboard and of textiles made from cotton, linen, and other plant fibres. Cellulose can be converted into cellophane, a thin transparent film, and into rayon, an important fibre that has been used for textiles since the beginning of the 20th century. Both cellophane and rayon are known as "regenerated cellulose fibres".

Cellulose fibres are also used in liquid filtration, to create a filter bed of inert material. Cellulose is further used to make hydrophilic and highly absorbent sponges.

For industrial use, cellulose is mainly obtained from wood pulp and cotton. It is mainly used to produce cardboard and paper; and to a smaller extent it is converted into a wide variety of derivative products.

Cellulose pulp as a raw material is processed out of wood or stems of plants such as hemp, linen and manila. Pulp fibres are built up mainly from cellulose and other organic components (hemicellulose and lignin). The cellulose macromolecules (composed of 1-4 glycosidic linked β-D-Glucose molecules) are linked together by hydrogen bonds to form a so called primary fibril (micelle) which has crystalline and amorphous domains. Several primary fibrils (around 55) form a so called microfibril. Around 250 of these microfibrils form a fibril.

The fibrils are arranged in different layers (which can contain lignin and/or hemicellulose) to form a fibre. The individual fibres are bound together by lignin as well.

The pulps used in papermaking are often obtained by grinding the wood and an optional processing by heat and chemistry to remove undesired compounds from the cellulosic fibres.

The fibres are ground and cut to a certain fineness (depending on the desired properties). The grinding of the fibres is achieved with a refiner (such as a conic rotor-stator mill or disc- or double-disc refiners). The refiner also fibrillates the fibres on the surface which means that some fibrils are partially pulled out of the surface of the fibre. This leads to a better retention of, and, frequently, adhesion to, pigments, which may be added in paper production, and also to an enhanced potential of hydrogen bonding between the fibres of the paper. This results in improved mechanical properties. A side-effect is also that the paper becomes denser and more transparent because of a loss of light scattering as the size of the scattering centres moves away from the accepted optimum of half the wave length of light (glassine and greaseproof papers).

When fibres become refined under applied energy they become fibrillated as the cell walls are broken and torn into attached strips, i.e. into fibrils. If this breakage is continued to separate the fibrils from the body of the fibre, it releases the fibrils. The breakdown of fibres into microfibrils is referred to as "microfibrillation". This process may be continued until there are no fibres left and only fibrils of nano size (thickness) remain.

If the process goes further and breaks these fibrils down into smaller and smaller fibrils, they eventually become cellulose fragments or nano-gel. Depending on how far this last step is taken some nano-fibrils may remain amongst the nano-fibril gel. The breakdown to primary fibrils may be referred to as "nano-fibrillation", where there may be a smooth transition between the two regimes. The primary fibrils form in an aqueous environment a gel (meta stable network of primary fibrils) which may be referred to as "nano-fibrillar gel". The gel formed from the nano-fibrils can be considered to contain nanocellulose.

Nano-fibrillar gels are desirable as they usually contain very fine fibrils, considered to be constituted in part of nanocellulose, showing a stronger binding potential to themselves, or to any other material present, than do fibrils which are not so fine or do not exhibit nanocellulosic structure.

The achievable fineness with conventional refiners however is limited. Also, a number of other apparati for breaking down particles are not capable of breaking down cellulose fibres to nano-fibrils, such as fluffers mentioned in US 2001/0045264, which are only capable of separating given size fractions of fibres from each other.

Similarly, in WO 02/090651 a method for recycling pulp rejects generated during manufacturing of paper, paperboard or cardboard is described, wherein cleaner rejects containing among other things fibres, pigments and/or fibres are milled to a certain grain size by ball mills. However, no mention is made of the fibrillation of the fibres present, let alone the fibrillation into nano-fibrils or a nano-fibrillar cellulose gel.

If a further breakdown of the fibres into fibrils or even in cellulose molecules is desired, other methods are needed.

For example, in U.S. Pat. No. 4,374,702 a process for preparing microfibrillated cellulose is described comprising passing a liquid suspension of fibrous cellulose through a high pressure homogenizer having a small diameter orifice in which the suspension is subjected to a pressure drop of at least 3000 psi and a high velocity shearing action followed by a high velocity decelerating impact against a solid surface, repeating the passage of said suspension through the orifice until said cellulose suspension becomes a substantially stable suspension, said process converting said cellulose into microfibrillated cellulose without substantial chemical change of the cellulose starting material. A nano-fibrillar cellulose gel is not mentioned.

U.S. Pat. No. 6,183,596 B1 discloses a process for producing super microfibrillated cellulose by passing a slurry of a previously beaten pulp through a rubbing apparatus having two or more grinders which are arranged so that they can be rubbed together to microfibrillate the pulp to obtain microfibrillated cellulose and further super microfibrillate the obtained microfibrillated cellulose with a high-pressure homogenizer to obtain the super microfibrillated cellulose. There is however no mention of a nano-fibrillar cellulose gel.

Furthermore, ultra-fine friction grinders can be used, wherein the grinder reduces the fibres into fines by mechanical shearing (cf. e.g. U.S. Pat. No. 6,214,163 B1), which however does not automatically lead to a nano-fibrillar cellulose gel.

The mechanical production of nano-fibrillar cellulose is not trivial. For example, there is a problem of increasing viscosity during the fibrillation process. This can stop the process completely or increase the needed specific energy.

Thus, there is still a need for a process for producing nano-fibrillar cellulose gels, which is not only easily carried out, but energy efficient.

It is one objective of the present invention to provide such process for the production of nano-fibrillar cellulose gels.

It has now been found that in machines, where the throughput is a function of viscosity, an advantageous decrease of the viscosity of nano-fibrillar cellulose gels is observed by the addition and co-processing of certain fillers and/or pigments with the cellulose fibre containing pulp resulting in a better throughput.

Thus, the above problem is solved by the process for the production of nano-fibrillar cellulose gels of the present invention.

This process is characterized by the following steps:
(a) providing cellulose fibres;
(b) providing at least one filler and/or pigment;
(c) combining the cellulose fibres and the at least one filler and/or pigment;
(d) fibrillating the cellulose fibres in the presences of the at least one filler and/or pigment until a gel is formed.

Nano-fibrillar cellulose in the context of the present invention means fibres, which are at least partially broken down to primary fibrils. If these primary fibrils are in an aqueous environment, a gel (meta stable network of primary fibrils considered in the limit of fineness to be essentially nanocellulose) is formed, which is designated as "nano-fibrillar gel", wherein there is a smooth transition between nano fibres and nano-fibrillar gel, comprising nano-fibrillar gels containing a varying extent of nano-fibrils, all of which are comprised by the term nano-fibrillar cellulose gels according to the present invention.

In this respect, fibrillating in the context of the present invention means any process which predominantly breaks down the fibres and fibrils along their long axis resulting in the decrease of the diameter of the fibres and fibrils, respectively.

According to the process of the present invention, the fibrillation of cellulose fibres in the presence of at least one filler and/or pigment provides a nano-fibrillar cellulose gel.

The fibrillation is performed until the gel is formed, wherein the formation of the gel is verified by the monitoring of the viscosity in dependence of the shearing rate. Upon step-wise increase of the shearing rate a certain curve reflecting a decrease of the viscosity is obtained. If, subsequently the shearing rate is step-wise reduced, the viscosity increases again, but the corresponding values over at least part of the shear rate range as shearing approaches zero are lower than when increasing the shearing rate, graphically expressed by a hysteresis in the of the viscosity plotted against the shearing rate. As soon as this behaviour is observed, a nano-fibrillar cellulose gel according to the present invention is formed.

Furthermore, during the fibrillation of the pulp in machines, where the throughput is a function of viscosity, the viscosity of the gel formed according to the present invention is preferably lower than the viscosity of a corresponding suspension of nano-fibrillar cellulose, having been fibrillated in the absence of fillers and/or pigments.

The Brookfield viscosity can be measured with any conventional Brookfield viscometer using routine operations known by the person skilled in the art.

Cellulose fibres, which can be used in the process of the present invention may be such contained in pulps selected from the group comprising *eucalyptus* pulp, spruce pulp, pine pulp, beech pulp, hemp pulp, cotton pulp, and mixtures thereof. In one embodiment, all or part of this cellulose fibre may be issued from a step of recycling a material comprising cellulose fibres. Thus, the pulp may also be recycled pulp.

The size of the cellulose fibres in principle is not critical. Useful in the present invention generally are any fibres commercially available and processable in the device used for their fibrillation. Depending on their origin, cellulose fibres may have a length of from 50 mm to 0.1 µm. Such fibres, as well as such having a length of preferably 20 mm to 0.5 µm, more preferably from 10 mm to 1 mm, and typically from 2 to 5 mm, can be advantageously used in the present invention, wherein also longer and shorter fibres may be useful.

It is advantageous for the use in the present invention that the cellulose fibres are provided in the form of a suspension, especially an aqueous suspension. Preferably, such suspensions have a solids content of from 0.2 to 35 wt-%, more preferably 0.25 to 10 wt-%, even more preferably 0.5 to 5 wt-%, especially 1 to 4 wt-%, most preferably 1.3 to 3 wt-%, e.g. 1.5 wt-%.

The at least one filler and/or pigment is selected from the group comprising precipitated calcium carbonate (PCC); natural ground calcium carbonate (GCC); dolomite; talc; bentonite; clay; magnesite; satinwhite; sepiolite, huntite, diatomite; silicates; and mixtures thereof. Precipitated calcium carbonate, which may have vateritic, calcitic or aragonitic crystal structure, and/or natural ground calcium carbonate, which may be selected from marble, limestone and/or chalk, are especially preferred.

In a special embodiment, the use of ultrafine discrete prismatic, scalenohedral or rhombohedral precipitated calcium carbonate may be advantageous.

The fillers and/or pigments can be provided in the form of a powder, although they are preferably added in the form of a suspension, such as an aqueous suspension. In this case, the solids content of the suspension is not critical as long as it is a pumpable liquid.

In a preferred embodiment, the filler and/or pigment particles have a median particle size of from 0.5 to 15 µm, preferably 0.7 to 10 µm, more preferably 1 to 5 µm and most preferably 1.1 to 2 µm, e.g. 1.5 µm or 3.2 µm.

Especially preferably, the filler and/or pigment particles have a median particle size of from 0.01 to 15 µm, preferably 0.1 to 10 µm, more preferably 0.3 to 5 µm and most preferably 0.5 to 4 µm.

For the determination of the weight median particle size $d_{50}$, for particles having a $d_{50}$ greater than 0.5 µm, a Sedigraph 5100 device from the company Micromeritics, USA was used. The measurement was performed in an aqueous solution of 0.1 wt-% $Na_4P_2O_7$. The samples were dispersed using a high-speed stirrer and ultrasound. For the determination of the volume median particle size for particles having a $d_{50} \leq 500$ nm, a Malvern Zetasizer Nano ZS from the company Malvern, UK was used. The measurement was performed in an aqueous solution of 0.1 wt % $Na_4P_2O_7$. The samples were dispersed using a high-speed stirrer and ultrasound.

The fillers and/or pigments may be associated with dispersing agents such as those selected from the group comprising homopolymers or copolymers of polycarboxylic acids and/or their salts or derivatives such as esters based on, e.g., acrylic acid, methacrylic acid, maleic acid, fumaric acid, itaconic acid, e.g. acryl amide or acrylic esters such as methylmethacrylate, or mixtures thereof alkali polyphosphates, phosphonic-, citric- and tartaric acids and the salts or esters thereof or mixtures thereof.

The combination of fibres and at least one filler and/or pigment can be carried out by adding the filler and/or pigment to the fibres in one or several steps. As well, the fibres can be added to the filler and/or pigment in one or several steps. The filler and/or pigment as well as the fibres can be added entirely or in portions before or during the fibrillating step. However, the addition before fibrillating is preferred.

During the fibrillation process, the size of the fillers and/or pigments as well as the size of the fibres can change.

Preferably, the weight ratio of fibres to fillers and/or pigments on a dry weight basis is from 1:33 to 10:1, more preferably 1:10 to 7:1, even more preferably 1:5 to 5:1, typically 1:3 to 3:1, especially 1:2 to 2:1 and most preferably 1:1.5 to 1.5:1, e.g. 1:1.

The dosage of filler and/or pigment may be critical. If there is too much of the filler and/or pigment, this may influence the formation of the gel. Thus, if no gel formation is observed in specific combination, it might be necessary to reduce the amount of filler and/or pigment.

Furthermore, in one embodiment, the combination is stored for 2 to 12 hours, preferably 3 to 10 hours, more preferably 4 to 8 hours, e.g. 6 hours, prior to fibrillating it, as this ideally results in swelling of the fibres facilitating the fibrillation.

Fibre swelling may be facilitated by storage at increased pH, as well as by addition of cellulose solvents like, e.g. copper(II)ethylenediamine, iron-sodium-tartrate or lithium-chlorine/dimethylacetamine, or by any other method known in the art.

Fibrillating is carried out by means of any device useful therefore. Preferably the device is a homogenizer. It may also be an ultra fine friction grinder as described in U.S. Pat. No. 6,214,163 or U.S. Pat. No. 6,183,596.

Suitable for the use in the present invention are any commercially available homogenizers, especially high pressure homogenizers, wherein the suspensions are pressed under high pressure through a restricted opening, which may comprise a valve, and are discharged from the restricted opening at high pressure against a hard impact surface directly in front of the restricted opening, thus reducing the particle size. The pressure may be generated by a pump such as a piston pump, and the impact surface may comprise an impact ring extending around the annular valve opening. Example for homogenizers which can be used in the present invention Ariete NS2006L of GEA Niro Soavi. However, inter alia, also homogenizers such as of the APV Gaulin Series, HST HL Series or the Alfa Laval SHL Series can be used.

Furthermore, devices such as ultra-fine friction grinders, e.g. a Super Mass Colloider, can be advantageously used in the present invention.

The present manufacturing process is especially advantageous with respect to its efficiency. As mentioned above, the known pulp suspensions or gels have the drawback to have a relatively high viscosity in the fibrillation process, often leading to a high energy consumption, which is undesirable from an economical as well as ecological point of view.

Generally, minimising the viscosity in the process allows for two benefits:

(i) the gel can be formed more efficiently, but, nonetheless, the viscosity will rise (on a lower level line) as the gel is formed progressively, (ii) an even more beneficial gel can be made in viscosity critical processes by running with the invention until viscosity again rises close to the running maximum workable in the process, which means that the progress to ever finer gel has gone further than previously could be achieved.

Thus, the total energy to be applied for achieving a certain viscosity is significantly higher for gels containing the same type and amount of pulp as the nano-fibrillar cellulose gels according to the present invention, but do not contain filler and/or pigment. The same applies to gels or suspensions of the same kind and amount of pulp, but wherein the filler and/or pigment was added after fibrillation.

Consequently, the efficiency of the nano-fibrillar cellulose gel with respect to the total energy consumption in order to achieve a certain Brookfield viscosity is higher than the efficiency of a corresponding nano-fibrillar cellulose gel or suspension having been fibrillated in the absence of fillers and/or pigments or a corresponding gel or suspension not containing filler and/or pigment.

Thus, it is a further aspect of the invention to provide a process for enhancing the efficiency of producing nano-fibrillar cellulose gels by preparing the nano-fibrillar gels by a process as described above.

Another aspect of the present invention is the nano-fibrillar cellulose gel obtained by the processes according to the invention, the efficiency of which with respect to the total energy consumption in order to achieve a certain Brookfield viscosity preferably is higher than the efficiency of a corresponding nano-fibrillar cellulose gel having been fibrillated in the absence of fillers and/or pigments or a corresponding gel not containing filler and/or pigment.

Due to their mechanical strength properties the nano-fibrillar cellulose gels can be advantageously used in applications such as in material composites, plastics, paints, rubber, concrete, ceramics, adhesives, food, or in wound-healing applications.

The figures described below, and the examples and experiments, serve to illustrate the present invention and should not restrict it in any way.

EXAMPLES

A) Rheological Characterization

Figure 1:
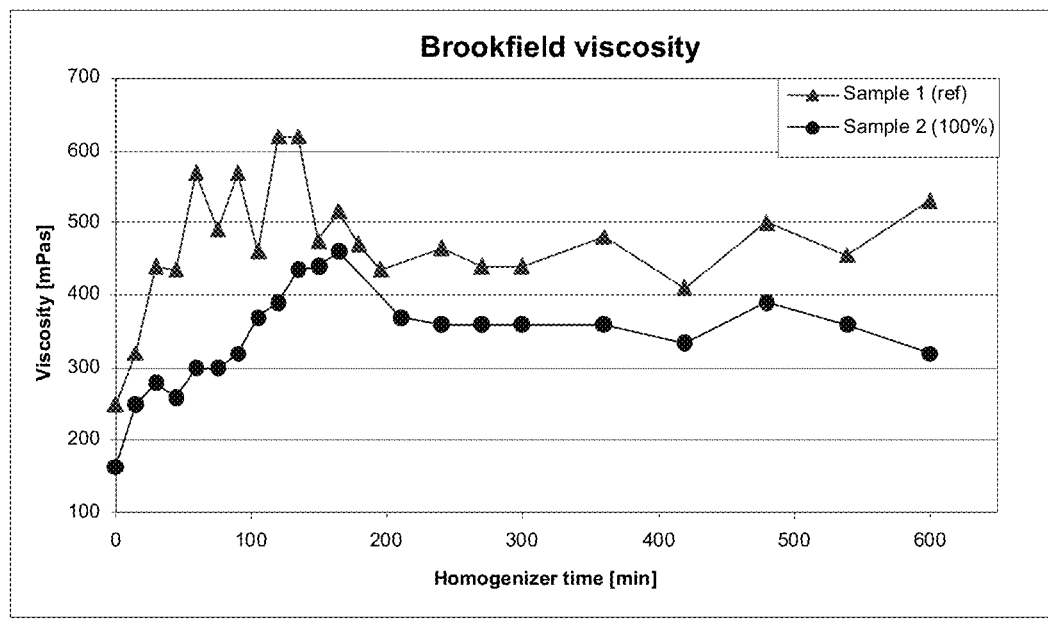
FIG. 1 shows the Brookfield viscosity progression during homogenizing of pulp mixtures with and without calcium carbonate.

For exemplifying the present invention, highly refined pulp (standard *eucalyptus* pulp with 20° SR refined to 80-83° SR using a pulp refiner used in paper plants) and a mixture of this pulp with a defined amount of carbonate (100 wt-% based on the dry weight fibres present, dry on dry (d/d), was fibrillated using a homogenizer. The pulp (reference) and the mixture were homogenized for 10 hours at around 1 000 bar pressure and viscosity measurements and SEM pictures were taken at defined time intervals.

The viscosity (at 50° C.) of the reference of 560 mPa·s after 10 hours homogenizing could be decreased to 435 mPa·s by co-homogenizing with 100 wt-% calcium carbonate (Omyacarb 1 AV) based on the dry weight fibres present.

In order to check whether the addition of calcium carbonate alone leads to a decrease of the viscosity of the homogenized pulp or the co-homogenizing is necessary, a sample of already homogenized pulp was mixed with calcium carbonate (100 wt-% calcium carbonate based on the dry weight fibres present, d/d), which is referred to as blend.

The viscosity of the "blend" (865 mPa·s) was higher than the viscosity of the co-homogenized mixture (435 mPa·s) and even higher than the viscosity of the homogenized reference (560 mPa·s) without calcium carbonate present.

Carbonate slurries with the same solids content but without homogenized pulp, on the other hand, do not show a significantly higher viscosity than the fibre-containing samples.

2. Material

Carbonate: Omyacarb 1 AV (GCC, solids content 100 wt-% based on weight of fibres present, weight median particle size $d_{50}=1.7$ μm measured by Sedigraph 5100) available from Omya AG Pulp: Standard *eucalyptus* pulp (20° SR) fibrillated to 80-83° SR using a refiner used in paper plants. The Schopper-Riegler degree (°SR) was measured according to the Zellcheming Merkblatt V/7/61 and standardized in ISO 5267/1.

3. Experimental Setup

3.1 Sample Preparation

For one homogenizer long term trial 1 000 g (solids content of about 3 wt-%) of the pulp as received was mixed with 1 250 g tap water using a stirrer (dissolver disc operating a rotation speed of 4 000 rpm) resulting in a solids content of about 1.3 wt-%. If necessary, the corresponding amount of calcium carbonate (Omyacarb 1 AV) was added while stirring further (cf. table 1). According amounts of this slurry were taken to perform viscosity experiments and SEM micrographs as described below. The rest of the slurry was transferred in the reservoir of the homogenizer. The samples which were used for the viscosity measurements were recycled in the process after performing the measurements.

TABLE 1

| Sample. No. | Calcium Carbonate | Amount [wt-%, d/d] | Starting solids content [wt-%] | Final solids content [wt-%] | Total time in homogenizer [h] |
|---|---|---|---|---|---|
| 1 | Omyacarb 1 AV | 0 | 1.3 | 1.7 | 10 |
| 2 | Omyacarb 1 AV | 100 | 2.6 | 2.4 | 10 |

3.2 Homogenizer

A homogenizer (GEA Niro Soavi; type NS 2006 L) was used for the fibrillation experiments. The reservoir was stirred with an external double propeller stirrer to prevent sedimentation of the slurry and to maintain a good conversion.

The machine was started with no pressure applied (the pistons on both homogenizing stages were completely pulled back) and the lowest pumping velocity. For adjusting the pressure of about 1 000 bar only the piston of the first stage was pushed in. The reaction time started when a pressure of 1 000 bar was achieved, wherein fluctuations of the pressure by ±200 bar were observed. Consistent under- or overpressure was compensated for by changing the position of the piston.

The slurry was held in circulation. Samples were taken out after the homogenizing chamber (before entering the reservoir again) to ensure at least one passage of the fibres through the homogenizing chamber.

4. Methods

4.1 Viscosity Measurements

4.1.1 Brookfield Viscosity

The viscosity measurements were performed on a Brookfield DV-II+ viscometer. The motor speed was set to 100 rpm and the viscosity was read out after 10, 60 and 600 seconds. The samples were measured either at room temperature or at 50° C. The samples were heated in a thermally controlled ultrasonic bath.

4.1.2 Rheology Measurements

Rheological measurements were performed using a Paar-Physika MCR 300 with the CC28.7 measuring system. The samples were measured at 20° C.

4.2 SEM

The scanning electron micrographs (SEM) were obtained by adding 0.5 g samples to 200 cm³ distilled water which then was filtered through a 0.8 μm pore nitrocellulose filter. The filter with overlying sample was dried in a vacuum drier. Preparations obtained on the membrane filter in this way were sputtered with 50 nm gold and evaluated in the SEM at various magnifications.

5. Results

5.1 Viscosity Measurements

From FIG. 1 the evolution of the viscosity (Brookfield) during homogenizing can be taken. The viscosity was read out after 600 seconds. The samples were measured at about 35° C. (which was the temperature of the samples taken directly after the homogenization chamber). Sample 1 is only pulp and therefore used as reference material for the calcium carbonate containing sample 2. As already mentioned, the viscosity increases during fibrillation. As can be seen, sample 2 containing 100 wt-% calcium carbonate (based on the dry weight fibres present; d/d) always had a lower viscosity than the reference, but also increases with increasing homogenization time.

For verifying whether the presence of calcium carbonate is necessary during the homogenizing for lowering the viscosity, also a blend of homogenized (10 h) sample 1 and 100 wt-% calcium carbonate (based on the dry weight fibres present; d/d) added after homogenization was produced and investigated. The viscosity was read out after 10, 60 and 600 seconds. The samples were heated in a thermally controlled ultrasonic bath and measured at 50° C.

Figure 2:
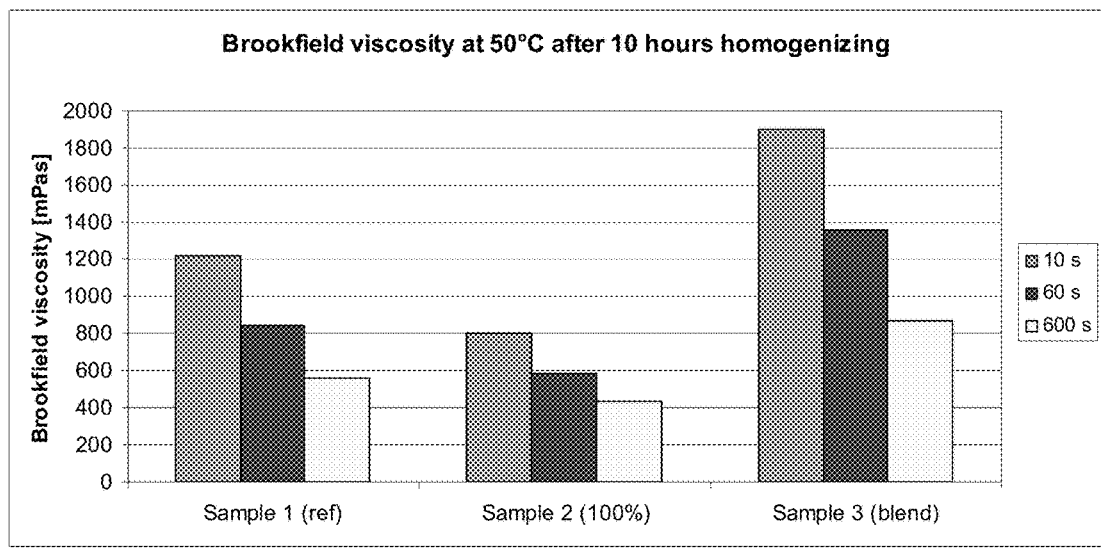
FIG. 2 shows the Brookfield viscosity of pulp mixtures with and without calcium carbonate, added before or after homogenization.

FIG. 2 shows the viscosities of pure homogenized pulp (sample 1), and pulp co-homogenized with 100 wt-% calcium carbonate (based on the dry weight fibres present; d/d) (sample 2), and mixtures of homogenized pulp and 100 wt-% calcium carbonate (based on the dry weight fibres present; d/d) added after homogenization (blend). In this respect, "10 s", "60 s" and "600 s" refer to the values of the Brookfield viscosity taken after 10, 60 and 600 seconds after the "power on" of the motor.

As can be seen, the co-homogenized mixture has a lower viscosity than the reference, whereas the blend has a higher viscosity than the corresponding co-homogenized mixture (sample 2) and the reference (sample 1).

Comparing the final viscosities (at 10 h homogenizing time) in FIG. 1 and in FIG. 2, slightly different values can be seen. This difference is accredited to the temperature dependence of the viscosity of the pulp mixtures.

5.2 Rheology Measurements

Figure 3:
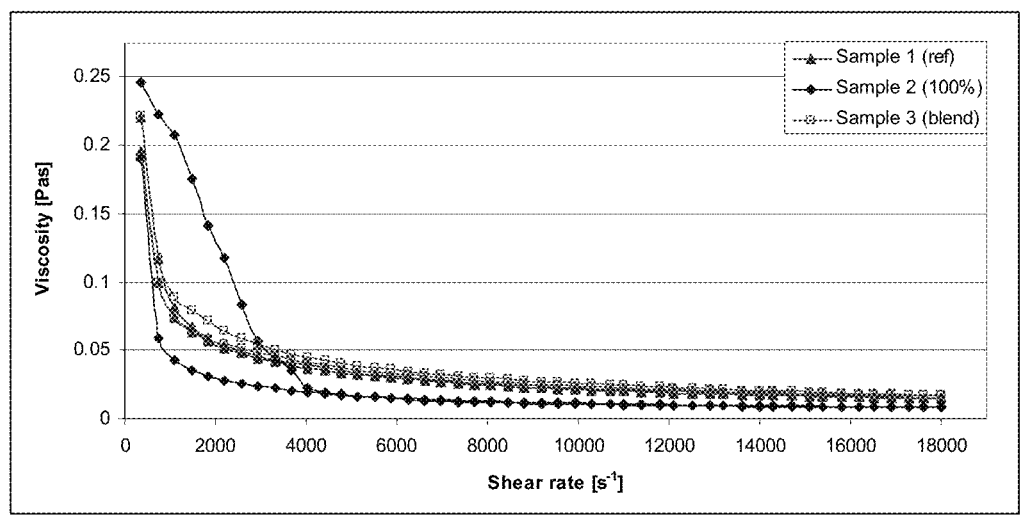
FIG. 3 shows the dependence of the viscosity of pulp mixtures with and without calcium carbonate added before or after homogenization on the shearing rate.

As one can see in FIG. 3, all the samples show a shear thinning behaviour. Table 2 shows the viscosities of the reference and the 100 wt-% calcium carbonate co-homogenized mixture and a 100 wt-% blend at 18 000 s$^{-1}$. Similar to the data of the Brookfield measurements (FIG. 2), the 100 wt-% carbonate co-homogenized has the lowest viscosity (8 mPa·s) and the 100 wt-% carbonate blend the highest viscosity (17 mPa·s).

TABLE 2

| Sample | Viscosity [mPa · s] at 18 000 s$^{-1}$ |
| --- | --- |
| Sample 1 (ref) | 14 |
| Sample 2 (co-homogenized with 100 wt.-% carbonate) | 8 |
| Sample 3 (blend with 100 wt.-% carbonate) | 17 |

Furthermore, it can clearly be taken from FIG. 3 that there is a hysteresis in the case of sample 2, representing the case of fibres co-homogenized with 100 wt.-% calcium carbonate.

At low shearing rates, the viscosity decreases progressively as shear is increased until a shearing rate of about 18 000 s$^{-1}$. Upon subsequently slowly decreasing the shearing rates, lower viscosities can be observed than at the corresponding shearing rates in the previous increasing step, wherein the viscosity now always remains lower than the viscosities in the previous step, and lower than the viscosity of the blend and the pulp only sample 1 under similar shear conditions.

This behaviour not only shows the low viscosities, which can be achieved according to the invention, but also is a clear indication of the formation of a gel.

5.3 SEM

Figure 4A:
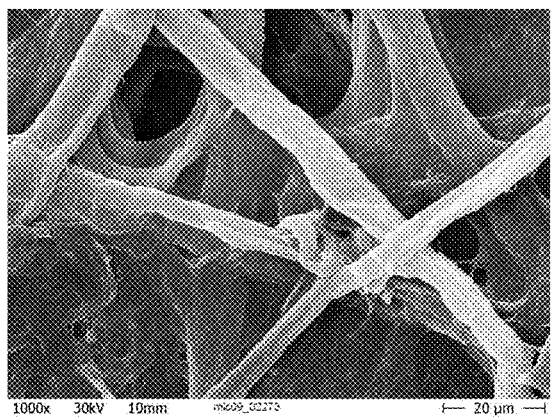
FIGS. 4a and b show SEM images of only fibres (FIG. 4a), fibres and 100 wt.-% calcium carbonate based on weight of fibres present before homogenization (FIG. 4b).
Figure 4B:
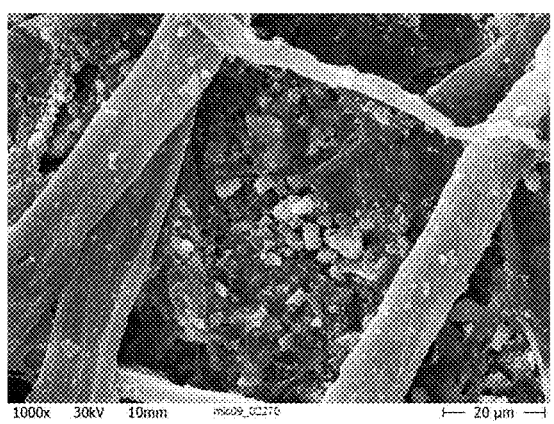
Figure 5A:
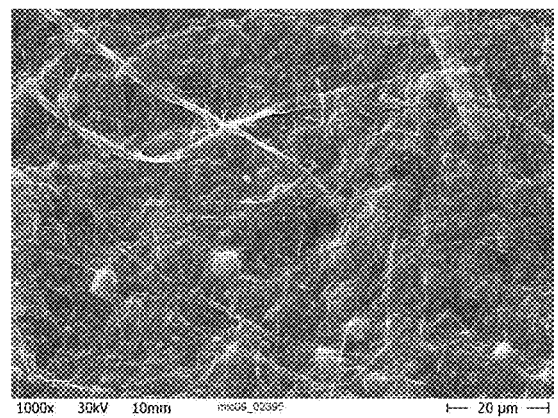
FIGS. 5a and b show SEM images of only fibres (FIG. 5a), fibres and 100 wt.-% calcium carbonate based on weight of fibres present after 2 hours of homogenization (FIG. 5b).
Figure 5B:
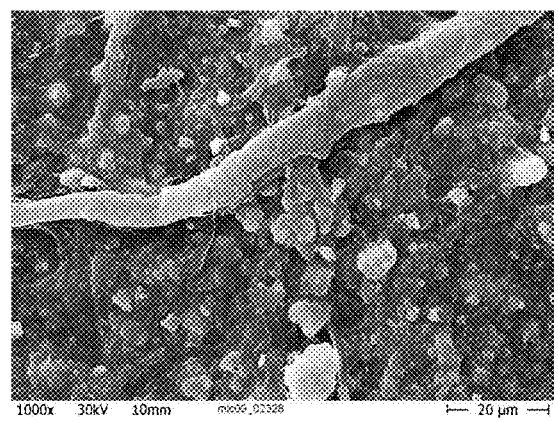
Figure 6A:
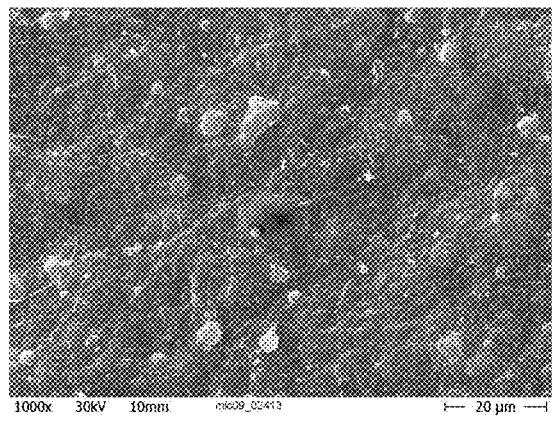
FIGS. 6a to b show SEM images of only fibres (FIG. 6a), fibres and 100 wt.-% calcium carbonate based on weight of fibres present after 10 hours of homogenization (FIG. 6b).
Figure 6B:
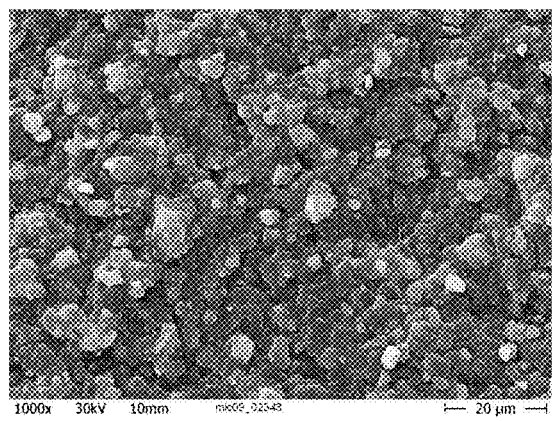
Figure 7:
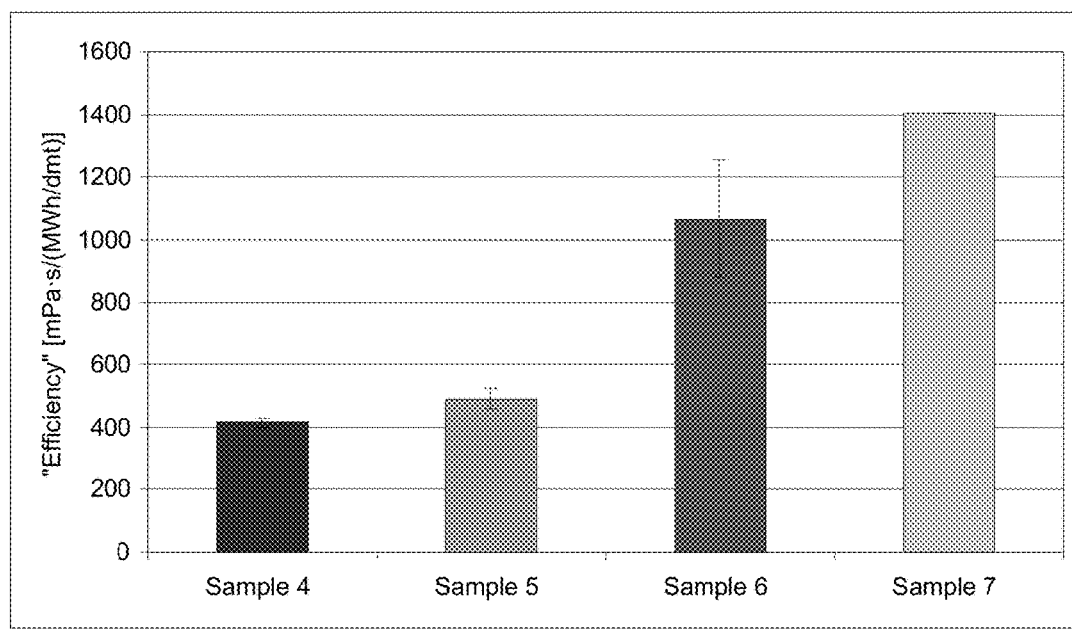
FIG. 7 shows the efficiency of gel formation of mixtures with and without calcium carbonate fillers.

Comparing FIG. 4a (referring to sample 1) and FIG. 4b (referring to sample 2) before homogenization, respectively, with FIGS. 5a and 5b after 2 hours homogenizing, respectively, and FIGS. 6a and 6b after 10 hours homogenizing, respectively, it can be seen that the pulp fibres become finer with increasing homogenizing time, and, without wishing to be bound to this theory, it appears that after a certain fineness of the fibrils is achieved they wrap around the carbonate particles and form a kind of layer on top of the carbonate particles.

B) Efficiency of Gel Formation

"Efficiency" in the context of the present invention is defined as the Brookfield viscosity (higher Brookfield viscosity means a more stable gel that means higher degree of fibrillation) achieved per specific energy consumption:

1. Processing

All Examples (samples 4-9) were processed with an ultra-fine friction grinder (Supermasscolloider from Masuko Sangyo Co. Ltd, Japan (Model MKCA 6-2) with mounted silicon carbide stones having a grit class of 46 (grit size 297-420 μm). The gap between the stones was adjusted to "−50" μm (dynamic 0-point, as described in the manual delivered by the supplier). The speed of the rotating grinder was set to 2500 rpm for passes 1-5, to 2000 rpm for passes 6 and 7, to 1500 rpm for passes 8 and 9, to 1000 rpm for passes 10 and 11, to 750 rpm for passes 12 and 13 and to 500 rpm for passes 14 and 15.

2. Energy Measurement

The Energy measurement was performed by installing an electric meter (ELKO Syteme AG, DIZ D665Di) between the main power supply and the transformer to measure the energy take up of the whole Supermasscolloider system (as delivered from the supplier). The electric meter sends one signal per Wh to a digital counter (Hengstler, tico 731) to be able to read out the energy consumption per pass at the end of a pass with an accuracy of one Wh.

3. Weight Measurements

The solids content was measured using a Mettler Toledo HB 43-S Halogen solids balance. The end total mass was measured using a Mettler PK 36 Delta Range balance. The initial dry mass is the sum of all dry weight-ins at the beginning of an experiment (detailed compositions can be found in the formulations of the single experiments)

4. Brookfield Viscosity Determination

Brookfield viscosity was measured with Brookfield Model DV-II+ Viscometer.

To have a better comparability of the Brookfield measurement data, the Brookfield viscosity was measured in a dilution row to calculate the Brookfield viscosity at a fixed solids content. Additionally it was defined that only the ratio of dry cellulosic content (originating from dry pulp) to water is taken as reference parameter for Brookfield viscosity. The following formula was used to calculate the cellulosic solids content (s.c.$_c$):

$$s.c._c = \frac{\frac{s.c.}{p_c + p_f}}{100 - \left(p_f \cdot \frac{s.c.}{p_c + p_f}\right)}$$

s.c.$_c$ : cellulosic solids content s.c. : measured solids content of a sample $p_c$ : part cellulosic content, per definition= 1

$p_f$ : parts filler, weight ratio to part cellulosic content

The standardized Brookfield viscosity BV$_{2\%}$ was determined by the following method:

1. The solids content and the Brookfield viscosity (100 rpm, measuring after 30 s) of the original product are measured.

2. Three dilutions of the original products are produced by adding according amounts of tap water of which the solids contents (weight in at least 10 g) and the Brookfield viscosities (100 rpm, measuring after 30 s) are measured.

3. An xy-scatter diagram (x: solids content, y: Brookfield viscosity) is made and the points are fitted with a power law curve (y=ax$^b$).

4. Use the parameters a and b to calculate the Brookfield viscosity at the standardized cellulosic solids content x$_s$ of 2 wt %

To correct the intrinsic influence of Omyacarb 1 AV (samples 5-7) on the Brookfield viscosity of gels, a comparative gel containing no filler (sample 4) was mixed with according amounts of Omyacarb 1 AV (to have similar ratios as in samples 5-7). The $BV_{2\%}$ of these mixtures was determined according to the above mentioned procedure and percentage corrections with reference to the gel containing no filler were calculated. The percentage corrections are: for 0.1 p (part by weight; d/d; cf. sample 5) filler: <0.1% (neglected), 3 p (parts by weight; d/d; cf. sample 6) filler: −14.5%, 10 p (part by weight; d/d; cf. sample 7) filler: −37.5%.

According corrections for samples 8 and 9 were not performed, such that the presented "efficiency" values described below will be overestimated in a range of about 15 to 20%)

5. Calculation of Specific Energy Consumption

The specific energy consumption per pass $E_n$ is calculated as follows:

$$E_n = \frac{E_n}{m_n}$$

$$m_n = m_1 - \frac{n}{14}(m_1 - m_{15})$$

$$m_{15} = \sigma \cdot M$$

$E_n$ : specific energy of pass $n$ [MWh/dmt]

$E_n$ : measured energy of pass $n$ [Wh]

$m_n$ : dry mass of pass $n$ [g]

$m_1$ : initial dry mass [g]

$m_{15}$ : end dry mass [g]

$n$ : pass number $\sigma$ : solids content of final mass [wt %]

$M$ : final total mass [g]

6. Calculation of "Efficiency"

"Efficiency" ($\varepsilon$) in the context of the present invention is defined as the Brookfield viscosity (higher Brookfield viscosity means a more stable gel that means higher degree of fibrillation) achieved per specific energy consumption:

$$\varepsilon = \frac{BV_{2\%}}{E_{1-15}}$$

$\varepsilon$ : "Efficiency" $\left[\frac{mPas}{MWh/dmt}\right]$ $BV_{2\%}$ : Brookfield viscosity at 2wt % solids [mPas]

$E_{1-15}$ : Total specific energy of one example [MWh/dmt]

7. Material

Omyacarb 1 AV: available from Omya AG; Fine calcium carbonate powder, manufactured from a high purity white marble; The weight median particle size $d_{50}$ is 1.7 μm measured by Sedigraph 5100.

Nano GCC: Natural ground calcium carbonate (marble from Vermont); Dispersed slurry (solids content 50 wt %); The volume median particle size $d_{50}$ is 246 nm measured by Malvern Zetasizer Nano ZS.

Finntalc F40: Finntalc F40 available from Mondo Minerals; Talc filler for paper and board.

Eucalyptus pulp: Dry mat, brightness: 88.77%, 17° SR
Pine pulp: Dry mat, brightness: 88.19%, 20° SR 8. Sample Preparation Sample 4 (Comparative):

180 g dry Eucalyptus pulp and 5820 g tap water were mixed using a Pendraulik stirrer at 2000 rpm with a mounted dissolver disk (d=70 mm) for at least 10 minutes. This mixture was processed with the Supermasscolloider as described above in the according paragraph. This example was performed three times to show its reproducibility.

Sample 5:

180 g dry Eucalyptus pulp, 5820 g tap water and 18 g Omyacarb 1 AV (10:1 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph. This example was performed three times to show its reproducibility.

Sample 6:

180 g dry Eucalyptus pulp, 5820 g tap water and 540 g Omyacarb 1 AV (1:3 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph. This experiment was performed two times to show its reproducibility.

Sample 7:

180 g dry Eucalyptus pulp, 5820 g tap water and 1800 g Omyacarb 1 AV (1:10 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph.

Sample 8:

180 g dry Pine pulp, 5820 g tap water and 180 g Finntalc F40 (1:1 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph.

Sample 9:

180 g dry Eucalyptus pulp, 5820 g tap water and 360 g Nano GCC (1:1 pulp to filler, dry/dry) were mixed using a Pendraulik stirrer at 2000 rpm with a mounted dissolver disk (d=70 mm) for at least 10 minutes. This mixture was processed with the Supermasscolloider as described above in the according paragraph.

9. Results

Samples 4-7:

When comparing samples 4-7 it is obvious that the efficiency increases for gels that were produced in the presence of more filler, namely by up to 250%. The efficiency gain has to be more than 15% compared to a gel that was formed in the absence of filler.

Samples 8 and 9:

Samples 8 and 9 did not undergo the Brookfield viscosity-correction due to the intrinsic Brookfield viscosity increase of filler addition (see section "Brookfield viscosity determination").

Figure 8:
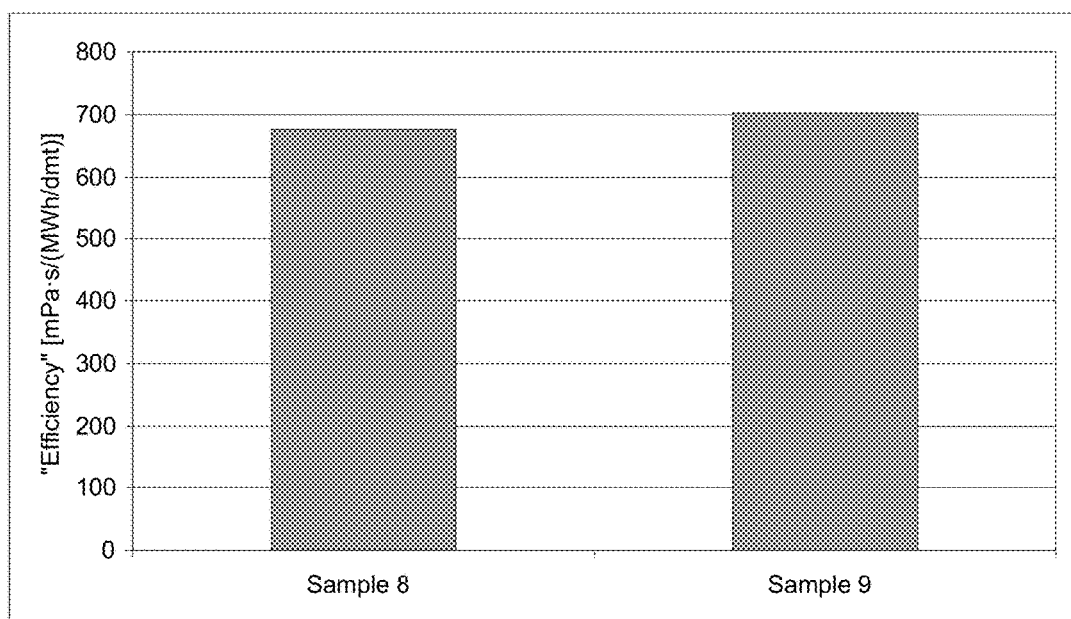
FIG. 8 shows the efficiency of gel formation of mixtures containing nanometer-sized calcium carbonate and talc as fillers.

However, as can be taken from FIG. 8, the efficiency is about 75% higher than the one of comparative sample 4, and still 40% higher if a correction of minus 20% of the measured efficiency value is assumed.

The invention claimed is:

1. A nano-fibrillar cellulose gel obtained by the process comprising the steps of:

(a) providing cellulose fibres contained in pulps selected from the group consisting of *eucalyptus* pulp, spruce pulp, pine pulp, beech pulp, hemp pulp, cotton pulp, or any mixture thereof;
(b) providing a filler;
(c) combining the cellulose fibres of step (a) and the filler; and
(d) fibrillating the cellulose fibres in an aqueous environment in the presence of the filler from step (c) until a nano-fibrillar cellulose gel is formed;
wherein the formation of the gel is verified by monitoring the viscosity of the mixture in dependence of the shearing rate, wherein the viscosity decrease of the mixture upon step-wise increase of the shearing rate is stronger than the corresponding viscosity increase upon subsequent step-wise reduction of the shearing rate over at least part of the shear rate range as shearing approaches zero;
wherein the filler is natural ground calcium carbonate, wherein in step (d) the weight ratio of fibres to filler on a dry weight basis is from 1:33 to 10:1, wherein the Brookfield viscosity of the nano-fibrillar cellulose gel formed in step (d) is lower than the Brookfield viscosity of a corresponding nano-fibrillar cellulose suspension having been fibrillated in the absence of the filler.

2. The gel according to claim 1, wherein the cellulose fibres in step (a) are provided in the form of a suspension.

3. The gel according to claim 1, wherein the cellulose fibres in step (a) are provided in the form of a suspension at a solids content of from 0.2 to 35 wt.-%.

4. The gel according to claim 1, wherein the cellulose fibres in step (a) are provided in the form of a suspension at a solids content of from 0.25 to 10 wt.-%.

5. The gel according to claim 1, wherein the cellulose fibres in step (a) are provided in the form of a suspension at a solids content of from 0.5 to 5 wt.-%.

6. The gel according to claim 1, wherein the cellulose fibres in step (a) are provided in the form of a suspension at a solids content of from 1 to 4 wt.-%.

7. The gel according to claim 1, wherein the cellulose fibres in step (a) are provided in the form of a suspension at a solids content of from 1.3 to 3 wt.-%.

8. The gel according to claim 1, wherein the filler in step (b) is natural ground calcium carbonate selected from marble, limestone and/or chalk.

9. The gel according to claim 1, wherein the filler in step (b) is in the form of particles having a median medium particle size of from 0.01 to 15 μm.

10. The gel according to claim 1, wherein the filler in step (b) is in the form of particles having a median medium particle size of from 0.1 to 10 μm.

11. The gel according to claim 1, wherein the filler in step (b) is in the form of particles having a median medium particle size of from 0.3 to 5 μm.

12. The gel according to claim 1, wherein the filler in step (b) is in the form of particles having a median medium particle size of from 0.5 to 4 μm.

13. The gel according to claim 1, wherein the filler in step (b) comprises a dispersing agent.

14. The gel according to claim 13, wherein the dispersing agent is selected from homopolymers or copolymers of polycarboxylic acids and/or their salts or esters, acrylic acid, methacrylic acid, maleic acid, fumaric acid, itaconic acid, acryl amide or acrylic esters, or mixtures thereof; alkali polyphosphates, phosphonic-, citric- and tartaric acids, salts or esters thereof; or mixtures thereof.

15. The gel according to claim 1, wherein in step (d) the weight ratio of fibres to filler on a dry weight basis is from 1:10 to 7:1.

16. The gel according to claim 1, wherein in step (d) the weight ratio of fibres to filler on a dry weight basis is from 1:5 to 5:1.

17. The gel according to claim 1, wherein in step (d) the weight ratio of fibres to filler on a dry weight basis is from 1:3 to 3:1.

18. The gel according to claim 1, wherein in step (d) the weight ratio of fibres to filler on a dry weight basis is from 1:2 to 2:1.

19. The gel according to claim 1, wherein in step (d) the weight ratio of fibres to filler on a dry weight basis is from 1:1.5 to 1.5:1.

20. The gel according to claim 1, wherein the fibrillating in step (d) is carried out by a homogenizer or an ultra fine friction grinder.

21. A material composite, plastic, paint, rubber, concrete, ceramic, adhesive, food or wound-healing composite comprising the nano-fibrillar cellulose gel according to claim 1.

* * * * *